(12) United States Patent
Austin et al.

(10) Patent No.: US 11,318,275 B2
(45) Date of Patent: May 3, 2022

(54) CONTROL FOR PRESSURE OF A PATIENT INTERFACE

(71) Applicant: ResMed Pty Ltd, Bella Vista (AU)

(72) Inventors: Benjamin Matthew Austin, Sydney (AU); Liam Holley, Sydney (AU)

(73) Assignee: ResMed Pty Ltd

( * ) Notice: Subject to any disclaimer, the term of this patent is extended or adjusted under 35 U.S.C. 154(b) by 1679 days.

(21) Appl. No.: 15/031,358

(22) PCT Filed: Oct. 28, 2014

(86) PCT No.: PCT/AU2014/050315
§ 371 (c)(1),
(2) Date: Apr. 22, 2016

(87) PCT Pub. No.: WO2015/061848
PCT Pub. Date: May 7, 2015

(65) Prior Publication Data
US 2016/0256660 A1  Sep. 8, 2016

(30) Foreign Application Priority Data

Oct. 30, 2013 (AU) ................................ 2013904199

(51) Int. Cl.
*A61M 16/20* (2006.01)
*A61M 16/00* (2006.01)
(Continued)

(52) U.S. Cl.
CPC ...... *A61M 16/202* (2014.02); *A61M 16/0051* (2013.01); *A61M 16/0069* (2014.02);
(Continued)

(58) Field of Classification Search
CPC ............ A61M 16/202; A61M 16/0069; A61M 16/0616; A61M 16/0627; A61M 16/0051; A61M 16/026; A61M 16/205
See application file for complete search history.

(56) References Cited

U.S. PATENT DOCUMENTS 4,944,310 A    7/1990  Sullivan
5,239,995 A *  8/1993  Estes ................... A61M 16/024
                                                 128/204.18
(Continued)

FOREIGN PATENT DOCUMENTS

WO    1998004310 A1    2/1998
WO    1998034665 A1    8/1998
(Continued)

OTHER PUBLICATIONS

International Search Report and Written Opinion for Application No. PCT/AU2014/050315 dated Feb. 23, 2015.
(Continued)

*Primary Examiner* — Margaret M Luarca
(74) *Attorney, Agent, or Firm* — Botos Churchill IP Law LLP

(57) ABSTRACT

A method of an apparatus control pressure in the patient interface. A vent valve may be used with a respiratory device, where the vent valve may selectively block fluid communication between components, such as the flow generator, the patient interface, and/or the vent. An expiratory flow model may be used to determine an expiratory characteristic such as an expiratory flow rate or pressure in the patient interface where an indicative measure may not be available. The expiratory flow model may receive inputs based on a measure of the patient's respiration, such as the tidal volume, peak inspiratory flow rate or length of inspiration. The expiratory characteristic may be used by a (Continued)

controller to control a pressure in the patient interface to provide respiratory therapy to a patient at or close to a target pressure.

29 Claims, 26 Drawing Sheets

(51) Int. Cl.
*A61M 16/06* (2006.01)
*A61M 16/16* (2006.01)
*A61M 16/10* (2006.01)

(52) U.S. Cl.
CPC ...... *A61M 16/026* (2017.08); *A61M 16/0616* (2014.02); *A61M 16/0627* (2014.02); *A61M 16/0683* (2013.01); *A61M 16/107* (2014.02); *A61M 16/1055* (2013.01); *A61M 16/16* (2013.01); *A61M 16/205* (2014.02); *A61M 2016/0021* (2013.01); *A61M 2016/0027* (2013.01); *A61M 2016/0036* (2013.01); *A61M 2202/0208* (2013.01); *A61M 2205/18* (2013.01); *A61M 2205/3584* (2013.01); *A61M 2205/502* (2013.01)

(56) References Cited

U.S. PATENT DOCUMENTS

| | | | | |
|---|---|---|---|---|
| 5,598,838 | A * | 2/1997 | Servidio | A61M 16/204 128/204.23 |
| 5,927,274 | A | 7/1999 | Servidio et al. | |
| 6,253,764 | B1 * | 7/2001 | Calluaud | A61M 16/202 128/204.18 |
| 6,305,372 | B1 | 10/2001 | Servidio | |
| 6,367,474 | B1 * | 4/2002 | Berthon-Jones | A61M 16/00 128/204.18 |
| 6,532,959 | B1 | 3/2003 | Berthon-Jones | |
| 6,581,594 | B1 | 6/2003 | Drew et al. | |
| 9,616,191 | B2 * | 4/2017 | Van Dijk | A61M 16/206 |
| 2009/0044808 | A1 | 2/2009 | Guney et al. | |
| 2009/0050156 | A1 | 2/2009 | Ng et al. | |
| 2010/0024824 | A1 * | 2/2010 | Chalvignac | A61M 16/206 128/205.24 |
| 2010/0269827 | A1 | 10/2010 | Rapoport | |
| 2013/0087146 | A1 * | 4/2013 | Callaghan | A61M 16/205 128/204.21 |
| 2013/0228180 | A1 * | 9/2013 | Ahmad | A61M 16/0069 128/204.23 |
| 2014/0283831 | A1 | 9/2014 | Foote et al. | |

FOREIGN PATENT DOCUMENTS

| | | |
|---|---|---|
| WO | 00078381 A1 | 12/2000 |
| WO | 2006074513 A1 | 7/2006 |
| WO | 2006079152 A1 | 8/2006 |
| WO | 2006102707 A1 | 10/2006 |
| WO | 2010121313 A1 | 10/2010 |
| WO | 2010135785 A1 | 12/2010 |
| WO | 2010141983 A1 | 12/2010 |
| WO | 2012024733 A2 | 3/2012 |
| WO | 2012171072 A1 | 12/2012 |
| WO | 2013040198 A2 | 3/2013 |
| WO | 2013067592 A1 | 5/2013 |
| WO | 2013152403 A1 | 10/2013 |

OTHER PUBLICATIONS

Written Opinion of the International Preliminary Examining Authority for Application No. PCT/AU2014/050315 dated Oct. 27, 2015.
International Preliminary Report on Patentability for Application No. PCT/AU2014/050315 dated Feb. 17, 2016.
Lorino, A.M., H. Lorino, and A . Harf. A synthesis of the Otis, Mead, and Mount mechanical respiratory models, Respiration Physiology 97(2:).: p. 123-133 including correction page.
Rodarte, J.R . and K. Rehder, Dynamics of Respiration, in Handbook of Physiology—The Respiratory System, 2011, Williams and Wilkins; Baltimore, p. 131-144.
Supplementary European Search Report for Application No. EP14857318 dated Jun. 23, 2017.

* cited by examiner

CONTROL FOR PRESSURE OF A PATIENT INTERFACE

1 CROSS-REFERENCE TO RELATED APPLICATION

This application is a national phase entry under 35 U.S.C. § 371 of International Application No. PCT/AU2014/050315, filed on Oct. 28, 2014, published in English, which claims priority to Australian Patent Application No. 2013904199, filed on Oct. 30, 2013, the disclosures of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders, and to procedures to prevent respiratory disorders. In particular, the present technology relates to respiratory devices, and their use for treating respiratory disorders and for preventing respiratory disorders.

2.2 Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body. The ventilator support is provided by a mask or nasal interface. NIV has been used to treat OHS, COPD, MD and Chest Wall disorders.

Invasive ventilation (IV) provides ventilatory support to patients that are no longer able to effectively breathe themselves and is provided using a tracheotomy tube.

Ventilators also control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, poorly fitting, difficult to use and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to effect a seal, or the mask may leak. Furthermore, if the shape of the seal-forming portion does not match that of the patient, it may crease or buckle in use, giving rise to leaks.

Another form of seal-forming portion may use adhesive to effect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

2.2.3.2 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed-partner 1100 of the patient 1000, e.g. through noise or focused airflow.

ResMed Limited has developed a number of improved mask vent technologies. See WO 1998/034,665; WO 2000/078.381; U.S. Pat. No. 6,581,594; US Patent Application; US 2009/0050156; US Patent Application 2009/0044808.

Table of noise of prior masks (ISO 17510-2:2007, 10 cmH$_2$O pressure at 1 m)

| Mask name | Mask type | A-weighted sound power level dbA (uncertainty) | A-weighted sound pressure dbA (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage (*) | nasal | 29.5 | 21.5 | 1998 |
| ResMed UltraMirage | nasal | 36 (3) | 28 (3) | 2000 |
| ResMed Mirage Activa | nasal | 32 (3) | 24 (3) | 2002 |
| ResMed Mirage Micro | nasal | 30 (3) | 22 (3) | 2008 |
| ResMed Mirage SoftGel | nasal | 29 (3) | 22 (3) | 2008 |
| ResMed Mirage FX | nasal | 26 (3) | 18 (3) | 2010 |
| ResMed Mirage Swift (*) | pillows | 37 | 29 | 2004 |
| ResMed Mirage Swift II | pillows | 28 (3) | 20 (3) | 2005 |
| ResMed Mirage Swift LT | pillows | 25 (3) | 17 (3) | 2008 |

(* one specimen only, measured using test method specified in ISO3744 in CPAP mode at 10 cmH$_2$O)

Sound pressure values of a variety of objects are listed below

| Object | A-Weighted sound pressure dbA (uncertainty) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

Many prior art vents are of a 'continuous' type. That is, these vents are continuously in fluid communication with the flow generator and the patient interface allow for gas to flow therethrough regardless of therapy condition. In some cases, certain aspects of continuous vents may be undesirable. One is that typically, any gas exhausted from the patient through the vent is of increased humidity in comparison to the ambient air. This may lead to additional drying of the patient's nasal passageways, or require additional water consumption from a humidifier where one is used.

Another undesirable aspect of a continuous vent may be that as continuous vents are always open, the blower typically needs to work harder to achieve the desired therapy pressure, for instance by operating at a higher rotational speed, to compensate for the leakage through the continuous vent. This may lead to lowered efficiencies in energy use, which may be important in circumstances where the PAP device is being powered by a battery. Higher blower operating speed may lead to an increased noise output, which may increase the level of disturbance to the patient. Increased blower rotation speed during operation may also have adverse effects on the life of the blower. In some cases, use of a continuous vent may require use of a larger blower to meet therapy flow or pressure requirements, as continuous vents may reduce the highest therapy pressure or flow that is able to be provided to the patient when using the blower.

Of course, some venting is required in order to wash out carbon dioxide that is exhaled by the patient.

2.2.4 Air Circuit 4170

An air circuit 4170 typically comprise at least one conduit or tube constructed and arranged to deliver a supply of air or breathable gas. Typically, an air circuit may be placed between a PAP device and a patient interface. If a humidifier is present then an air circuit may be placed between the humidifier and a PAP device, and/or between a humidifier and a patient interface. In particular, the air circuit may be in fluid communication with the outlet of the pneumatic block and the inlet to the patient interface to deliver a supply of breathable gas from the PAP device to the patient in use. The air circuit may be referred to as an air delivery tube. In such arrangements the air circuit may comprise a single limb or single conduit. Patient expired gas may be vented via an intentional leak vent or via a proximal pneumatic valve.

In other cases a double limb air circuit may be provided where separate conduits or limbs are provided for inhalation and exhalation. Such a double limb circuit comprises two conduits or tubes: an inspiratory tube that delivers air from the PAP device to the patient during inspiration; and an expiratory tube that delivers expired air from the patient to an expiratory port of the PAP device and then out an exhaust port. Geometrically the two tubes may be arranged side-by-side, in-line or co-axially. Air flow between the expiratory port and the exhaust port may be regulated by a pneumatic valve located internally within the PAP device.

Heated single limb or double limb air delivery circuits may also be used to prevent rainout from occurring within the air delivery circuits.

2.2.5 PAP Device

The air at positive pressure may be supplied to the airway of a patient by a PAP device such as a motor-driven blower. The outlet of the blower is connected via an air circuit to a patient interface as described above. It is to be understood that a PAP device includes any device configured to provide a supply of pressurized breathable gas for providing CPAP, invasive or non-invasive respiratory therapy including but not limited to a CPAP device, Bi-level PAP device and a ventilator.

2.2.6 Humidifier

Respiratory apparatuses commonly have the ability to alter the humidity of the breathable gas in order to reduce drying of the patient's airway and consequent patient discomfort and associated complications. The use of a humidifier placed between the flow generator or PAP device or ventilator and the patient interface produces humidified gas that minimizes drying of the nasal mucosa and increases patient airway comfort. In addition in cooler climates, warm air applied generally to the face area in and about the patient interface is more comfortable than cold air.

Humidity refers to the quantity of water vapour present in the air. It is commonly measured in two ways:
 (1) Absolute Humidity (AH) is the actual content of water recorded in terms of weight per volume—usually in grams per cubic meter (g/m3) or milligrams per liter (mg/L).
 (2) Relative Humidity (RH) is a percentage expression of the actual water vapour content of a gas compared to its capacity to carry water at any given temperature.

The capacity of air to hold water vapour increases as the temperature of the air increases. This means that for air with a stable AH, the RH will decline as the temperature of the air is increased. Conversely, for air saturated with water (100% RH), if the temperature is reduced then the excess water will condense out. Air breathed by humans is generally naturally heated and humidified by the airway to reach a temperature of 37° C. and 100% humidity. At this temperature the AH humidity is 44 mg/L.

Respiratory humidifiers are available in many forms and may be a standalone device that is coupled to a respiratory device via an air delivery tube, is integrated with the respiratory device or configured to be directly coupled to the relevant respiratory apparatus. While passive humidifiers can provide some relief, generally a heated humidifier is required to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or PAP device, and a gas outlet adapted to be connected to an air delivery conduit that delivers the humidified gas to the patient interface.

3 BRIEF SUMMARY OF THE TECHNOLOGY

The present technology is directed towards providing respiratory devices, such as medical devices, used in the diagnosis, amelioration, treatment, or prevention of respiratory disorders having one or more of improved comfort, cost, efficacy, ease of use and manufacturability.

A method of controlling pressure or determining pressure control values for control of pressure in the patient interface is disclosed. A vent valve may be used with a respiratory device, where the vent valve may selectively block fluid communication between components, such as the flow generator, the patient interface, and/or the vent. An expiratory flow model may be used to determine an expiratory characteristic such as an expiratory flow rate or pressure in the patient interface where an indicative measure may not be available. The expiratory flow model may receive inputs based on a measure of the patient's respiration, such as the tidal volume, peak inspiratory flow rate or length of inspiration. The expiratory characteristic may be used by a controller to control a pressure in the patient interface to provide respiratory therapy to a patient at or close to a target pressure.

Some versions of the present technology may include an apparatus for controlling a supply of breathable gas at a positive pressure for amelioration or treatment of a respiratory disorder. The apparatus may include a controller adapted to control setting of a therapy apparatus for providing a supply of breathable gas. The therapy apparatus may be adapted to couple with a patient interface to deliver the supply of breathable gas to an airway of a patient. The patient interface may be adapted with (a) a valve configured to selectively block fluid communication between a blower of the therapy apparatus and the patient interface, and (b) a vent to exhaust a flow of exhaust gas from the patient interface. The controller may be configured to determine an expiratory characteristic. It may also be configured to adjust a first pressure in the patient interface based on the expiratory characteristic by controlling the valve.

In some cases, the apparatus may further include the valve. The valve may include a movable portion to selectively block fluid communication between the blower and the patient interface. The movable portion may be configured to be movable by an actuator. The movable portion may be configured to be movable by a pressure difference acting on the movable portion. The movable portion may include or be a membrane. Optionally, the expiratory characteristic may be an estimate of expiratory flow rate, an estimate of pressure in the patient interface or a phase of expiration. The expiratory characteristic may be determined based on an expiratory flow model. The expiratory flow model may include one or a combination of a look-up table or a mathematical relationship or function. In some cases, the patient interface may be configured to deliver the supply of breathable gas to an airway of a patient; and the vent may be configured to exhaust a flow of exhaust gas from the patient interface. The valve may be further configured to selectively block fluid communication between the patient interface and the vent. The valve may be further configured to selectively block fluid communication between the blower and the patient interface or the patient interface and the vent. The apparatus may further include a flow generator configured to generate the supply of breathable gas at a second pressure. The first pressure may be adjusted by changing an output of the blower. The output of the blower may be the second pressure. Optionally, the expiratory characteristic may be determined based on one or more of: a ventilation volume, a tidal volume, a peak inspiratory flow, a length of time in inspiration, a lung compliance, a lung resistance, an end of inspiration or a start of expiration. The expiratory characteristic may be determined using a measure of respiration.

Some versions of the present technology may involve a control method in a processor for determining a pressure adjustment in a patient interface that delivers a supply of air or breathable gas to entrance of a patient's airways. The control method may include, in a presence of a selective blocking of fluid communication between a blower and a patient interface, determining an expiratory characteristic. The method may include determining an adjustment for a first pressure in the patient interface based on the expiratory characteristic.

Some versions of the present technology may include an apparatus for controlling a supply of breathable gas at a positive pressure for treatment of a respiratory disorder. The apparatus may include a controller, such as including at least one processor, adapted to control setting of a blower of a therapy apparatus for controlling a supply of breathable gas at a controlled pressure above ambient in a patient interface. The controller may be adapted to couple with at least one sensor for the therapy apparatus. The at least one sensor may be configured to measure pressure through a conduit from the therapy apparatus to the patient interface. The conduit may be in fluid communication with the patient interface configured to deliver the supply of breathable gas to an airway of a patient. The controller may be further configured to determine gas pressure in the patient interface in presence of, for example cyclical, blocking and unblocking of the conduit to the sensor. The determination of the gas pressure in the patient interface may involve a first unblocked-conduit process and a second blocked-conduit process, such as where the sensor may and may not accurately measure the pressure of the patient interface respectively.

In some cases, the first process may determine the patient interface gas pressure from a current measure of pressure from the sensor in presence of unblocking of the conduit to the sensor. The first process may determine the patient interface gas pressure from a pressure drop associated with a delivery conduit characteristic and the current measure of pressure. The first process may determine a pressure adjustment for pressure in the patient interface from a difference between the determined patient interface gas pressure and a target pressure.

In some cases, the second process may determine the patient interface gas pressure from or based on a modelled flow estimate in presence of blocking of the conduit to the sensor. The modelled flow estimate may be an estimate of expiratory flow. The determined patient interface gas pressure may be calculated from an elapsed time and the expiratory flow estimate. The second process may determine the elapsed time by detecting an end of inspiration, such as with an analysis of a measure from the sensor. The second process may determine a pressure adjustment for pressure in the patient interface from a difference between the determined patient interface gas pressure and a target pressure. The controller may be further configured for cyclical selection of the first process and the second process. The controller may select the first process upon determination of patient inspiration. The controller may select the second process upon determination of patient expiration. The controller may be further configured to determine an unintentional leak flow by subtracting a magnitude of patient flow at determined point of inflection from a total flow. The therapy apparatus may include the blower and the sensor. The apparatus may include the patient interface and the conduit. The apparatus may include a valve configured to selectively block expiratory gas communication to the sensor.

Some versions of the present technology involve a method of a processor to control setting of a blower of a therapy apparatus for providing a supply of breathable gas to a patient interface at a controlled pressure. The method may include, with a sensor of the therapy apparatus, measuring a pressure through a conduit from the therapy apparatus to the patient interface, the conduit in fluid communication with the patient interface. The method may further include determining in a first unblocked-conduit process and a second blocked-conduit process a patient interface gas pressure for control of the blower in presence of blocking and unblocking of the conduit to the sensor.

The first process may determine the patient interface gas pressure from a current measure of pressure from the sensor in presence of unblocking of the conduit to the sensor. The first process may determine the patient interface gas pressure from a pressure drop associated with a delivery conduit characteristic and the current measure of pressure. The first process may determine a pressure adjustment for pressure in the patient interface from a difference between the determined patient interface gas pressure and a target pressure.

The second process may determine the patient interface gas pressure from a modelled flow estimate in presence of blocking of the conduit to the sensor. The modelled flow estimate may be an estimate of expiratory flow. The determined patient interface gas pressure may be calculated from an elapsed time and the expiratory flow estimate. The second process may determine the elapsed time by detecting an end of inspiration. The second process may determine a pressure adjustment for pressure in the patient interface from a difference between the determined patient interface gas pressure and a target pressure. The method may include cyclically selecting the first process and the second process. In some cases, the first process may be selected upon determination of patient inspiration. In some cases, the second process may be selected upon determination of patient expiration. The method may further include determining an unintentional leak flow by subtracting a magnitude of patient flow at determined point of inflection from a total flow. In some cases, the patient interface may include a valve configured to selectively block expiratory gas communication to the sensor.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system in accordance with the present technology. A patient 1000 wearing a patient interface 3000, shown in the form of nasal pillows mask, receives a supply of air at positive pressure from a PAP device 4000. Air from the PAP device is humidified in a humidifier 5000, and passes along an air circuit 4170 to the patient 1000.

4.2 Therapy

4.2.1 Respiratory System

Figure 2A:
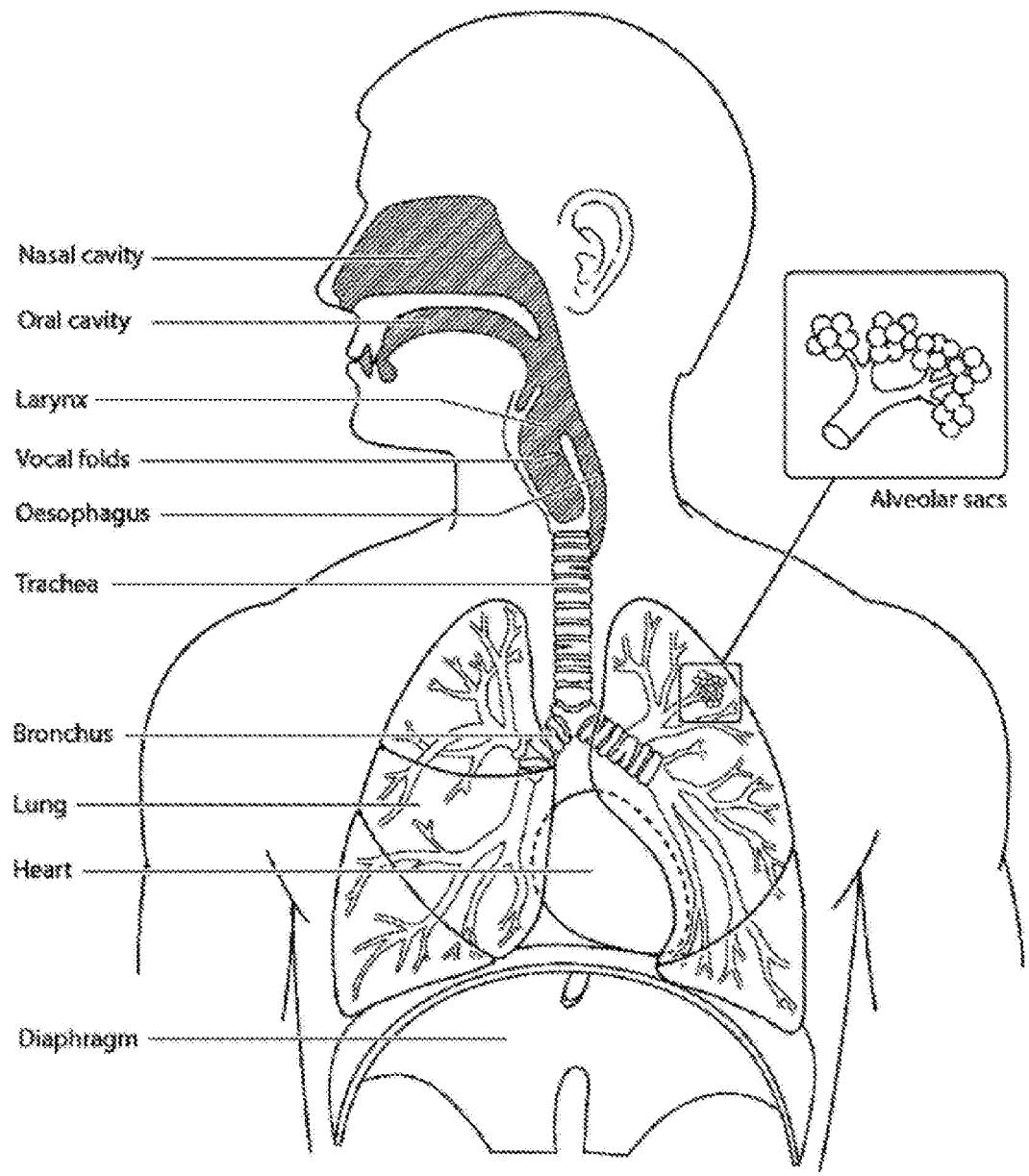

FIG. 2A shows an overview of a human respiratory system including the nasal and oral cavities, the larynx, vocal folds, oesophagus, trachea, bronchus, lung, alveolar sacs, heart and diaphragm.

Figure 2B:
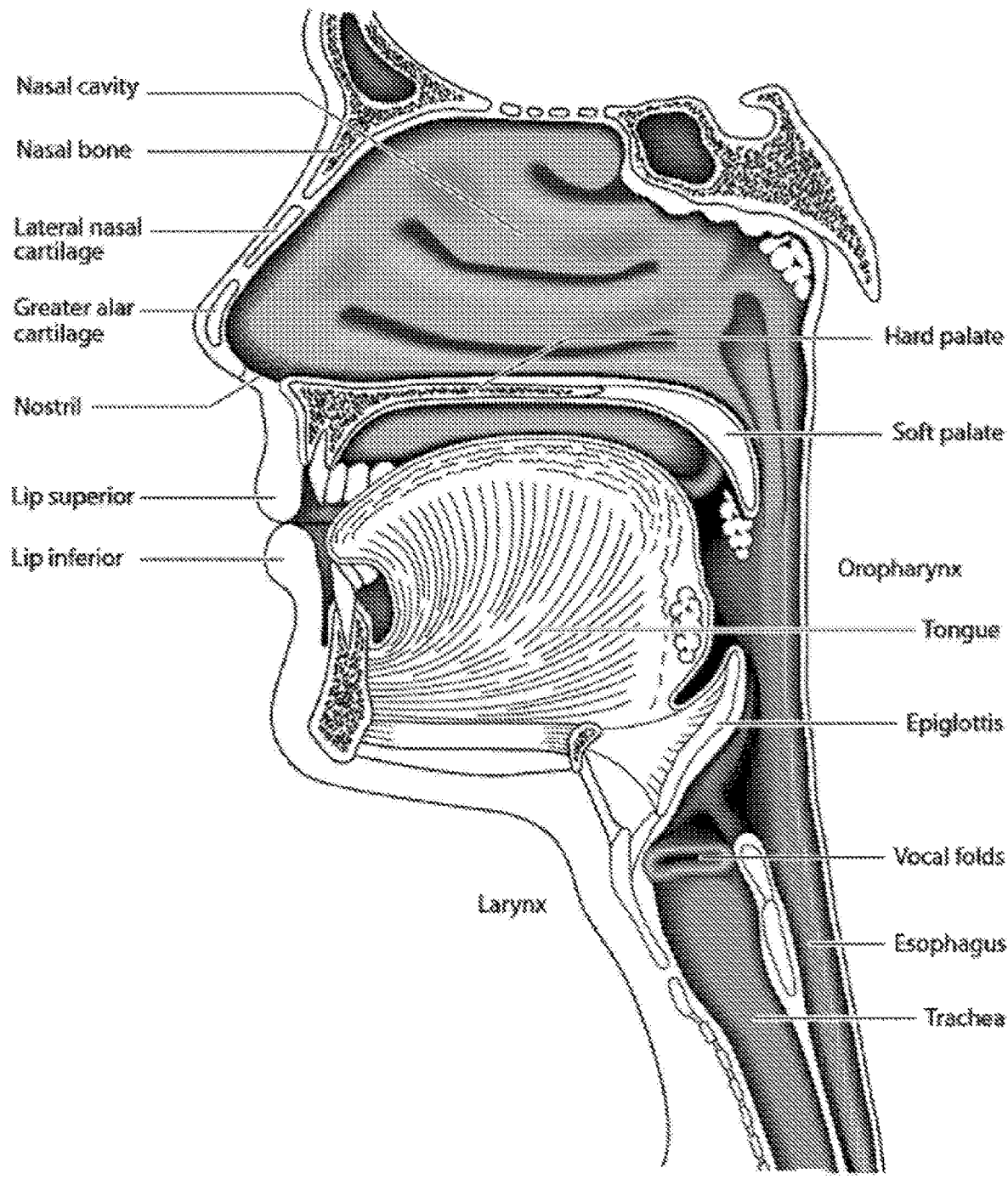

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.3 Patient Interface

Figure 3A:
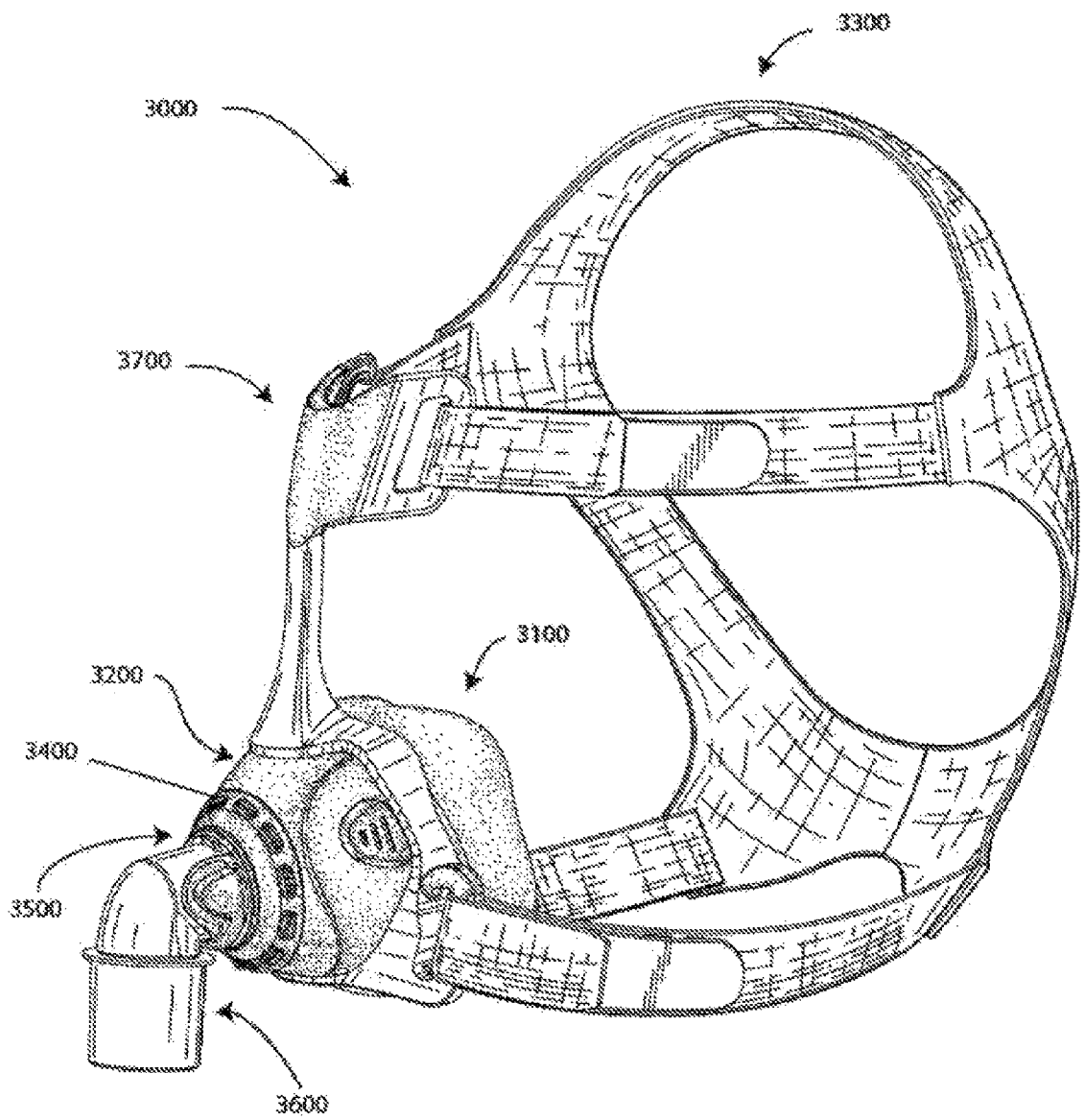

FIG. 3A shows a patient interface in accordance with one form of the present technology.

4.4 Pap Device

Figure 4A:
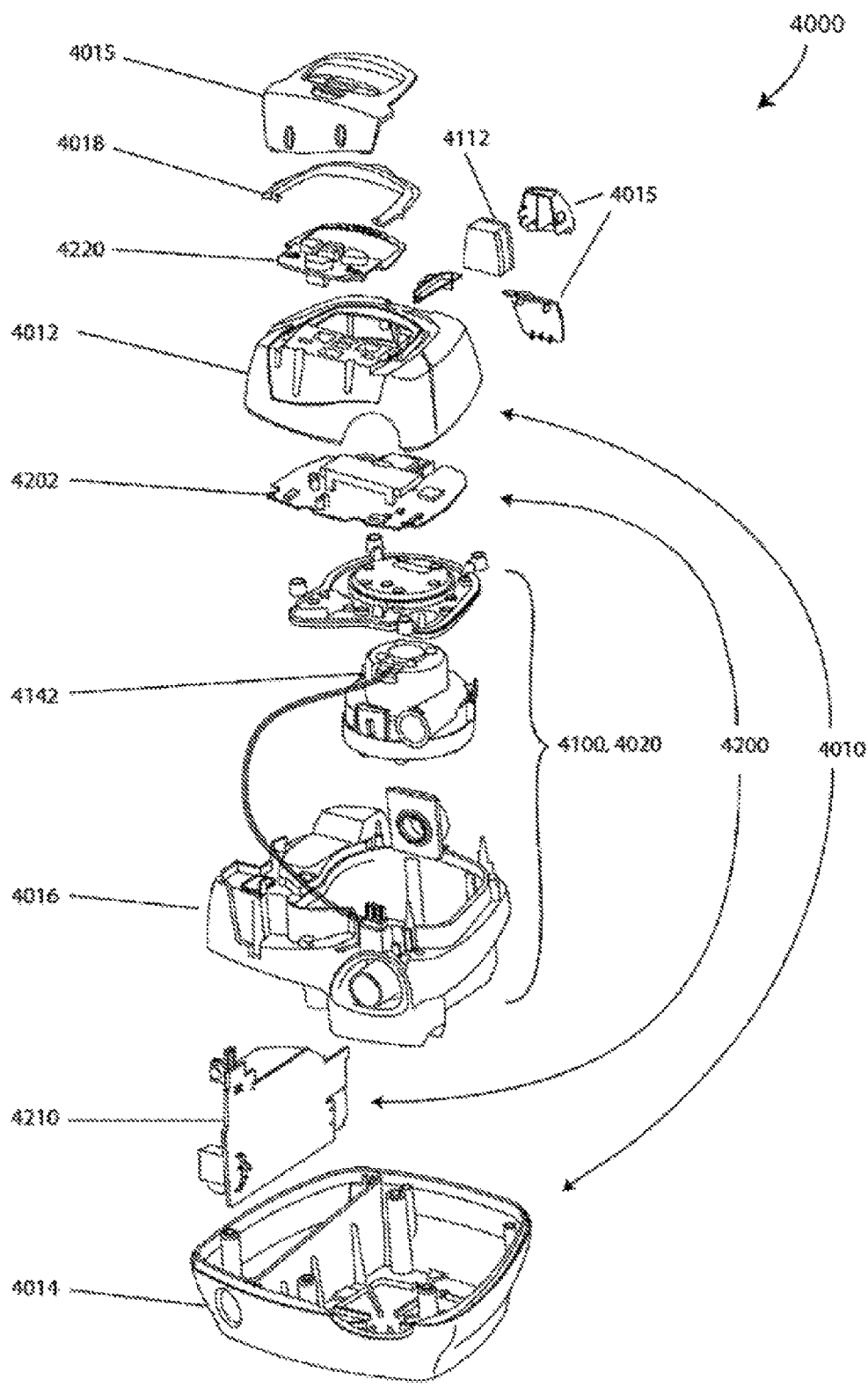

FIG. 4A shows an exploded view of a PAP device in accordance with one form of the present technology.

Figure 4B:
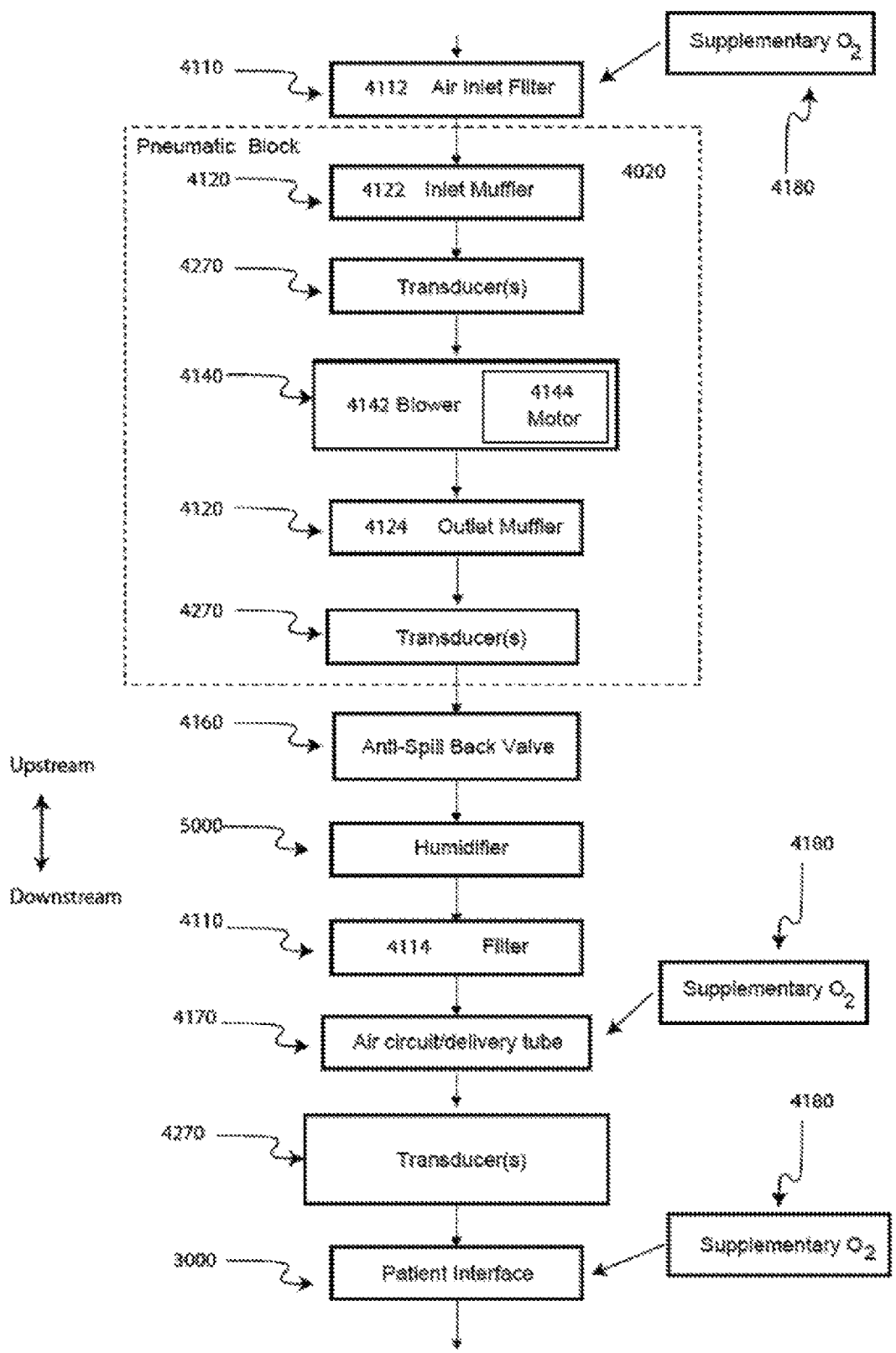

FIG. 4B shows a schematic diagram of the pneumatic circuit of a PAP device in accordance with one form of the present technology. The directions of upstream and downstream are indicated.

Figure 4C:
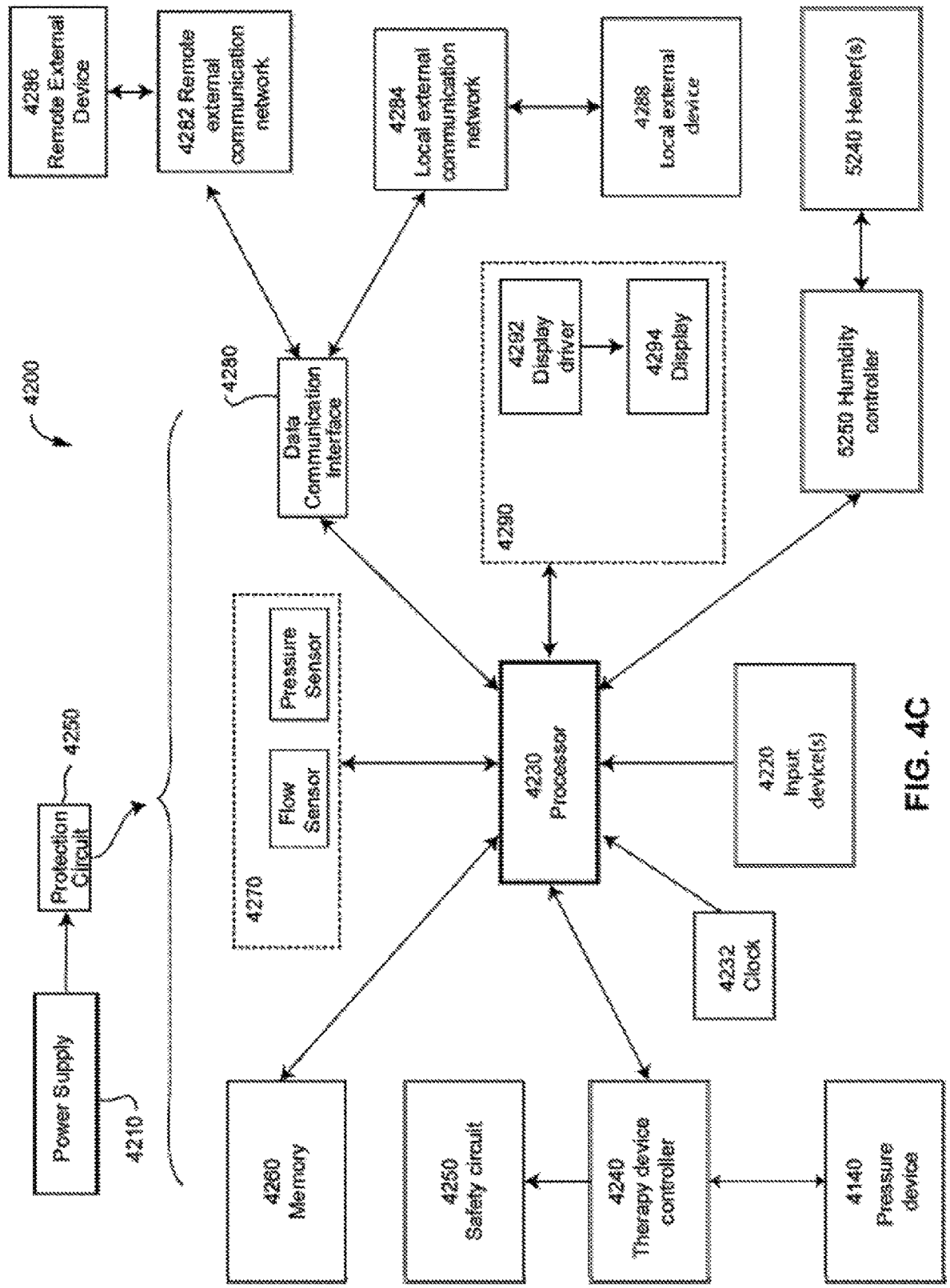

FIG. 4C shows a schematic diagram of the electrical components of a PAP device in accordance with one aspect of the present technology.

Figure 4D:
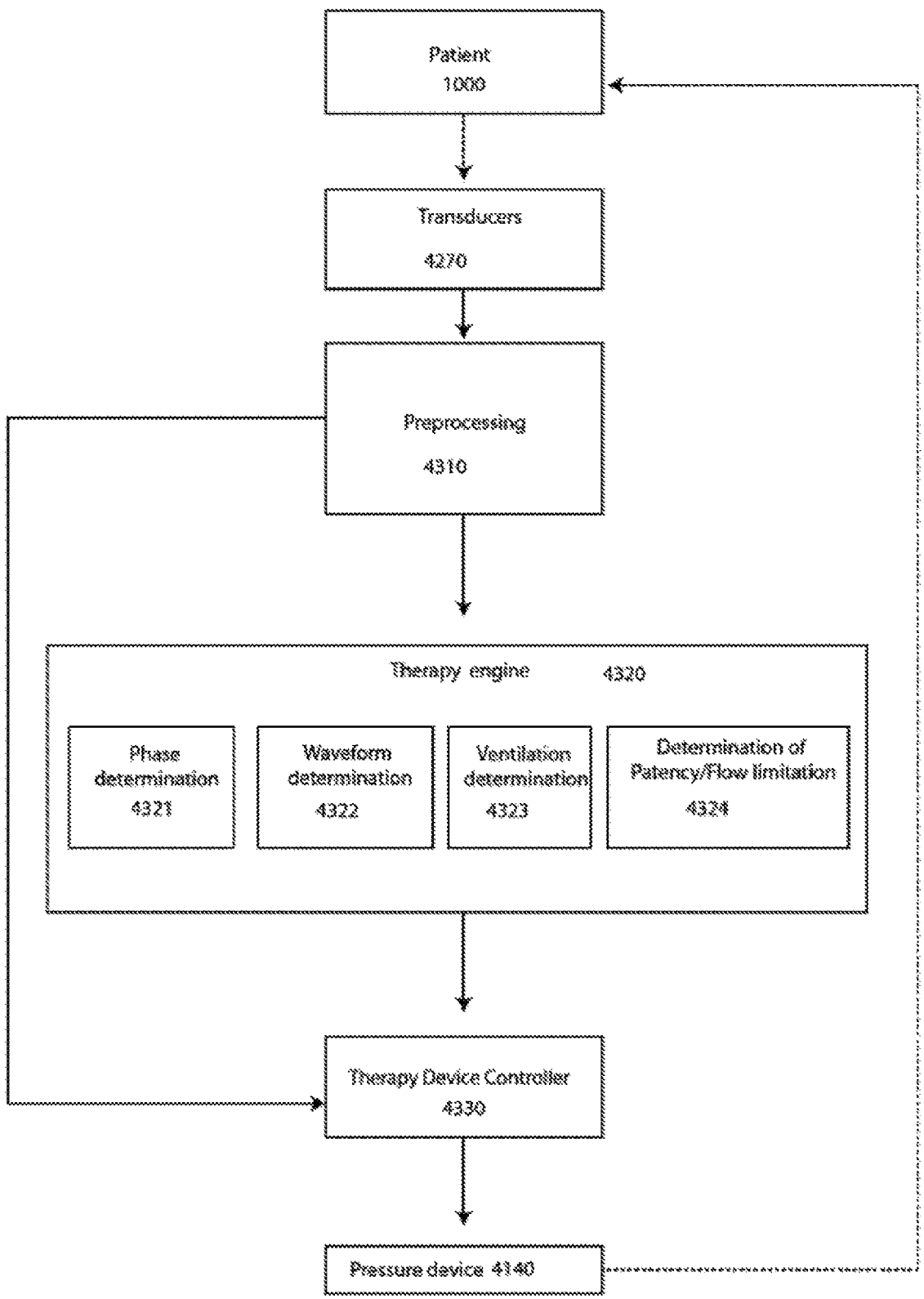

FIG. 4D shows a schematic diagram of the algorithms implemented in a PAP device in accordance with an aspect of the present technology. In this figure, arrows with solid lines indicate an actual flow of information, for example via an electronic signal.

Figure 4E:
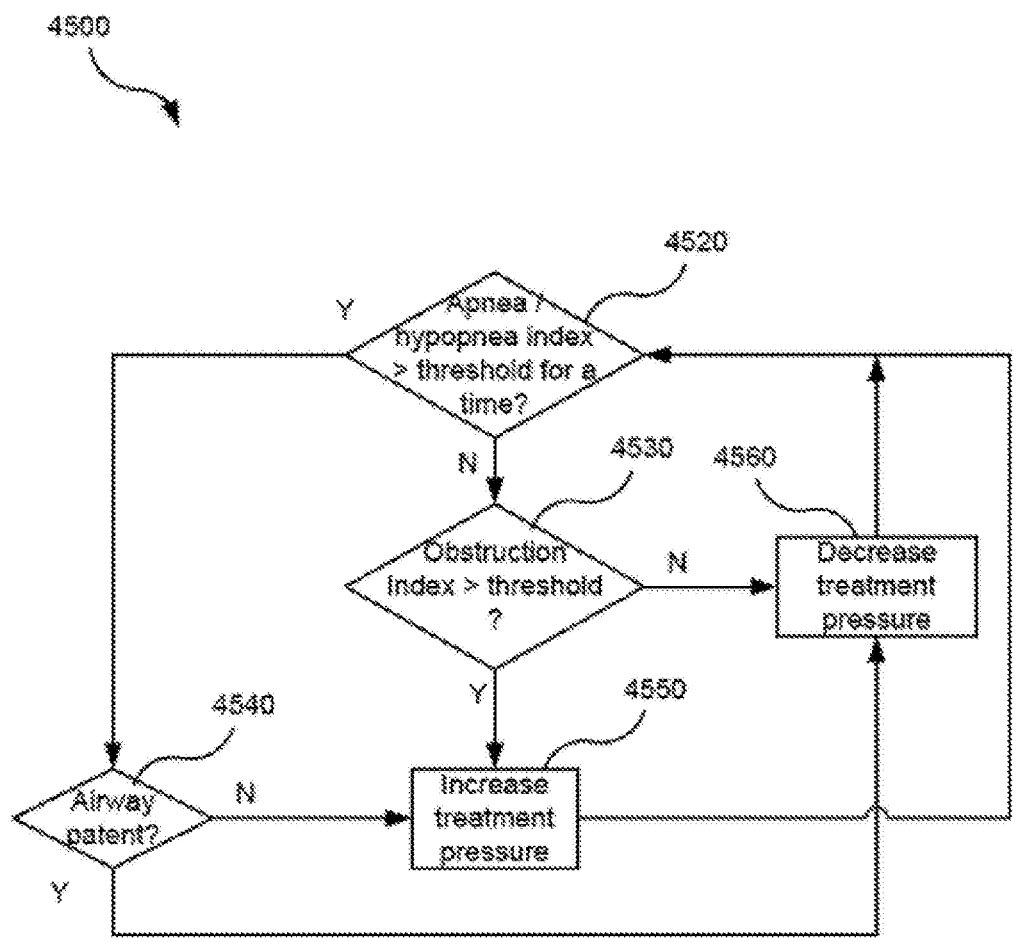

FIG. 4E is a flow chart illustrating an example method carried out by the therapy engine of FIG. 4D in accordance with one aspect of the present technology.

4.5 Humidifier

Figure 5A:
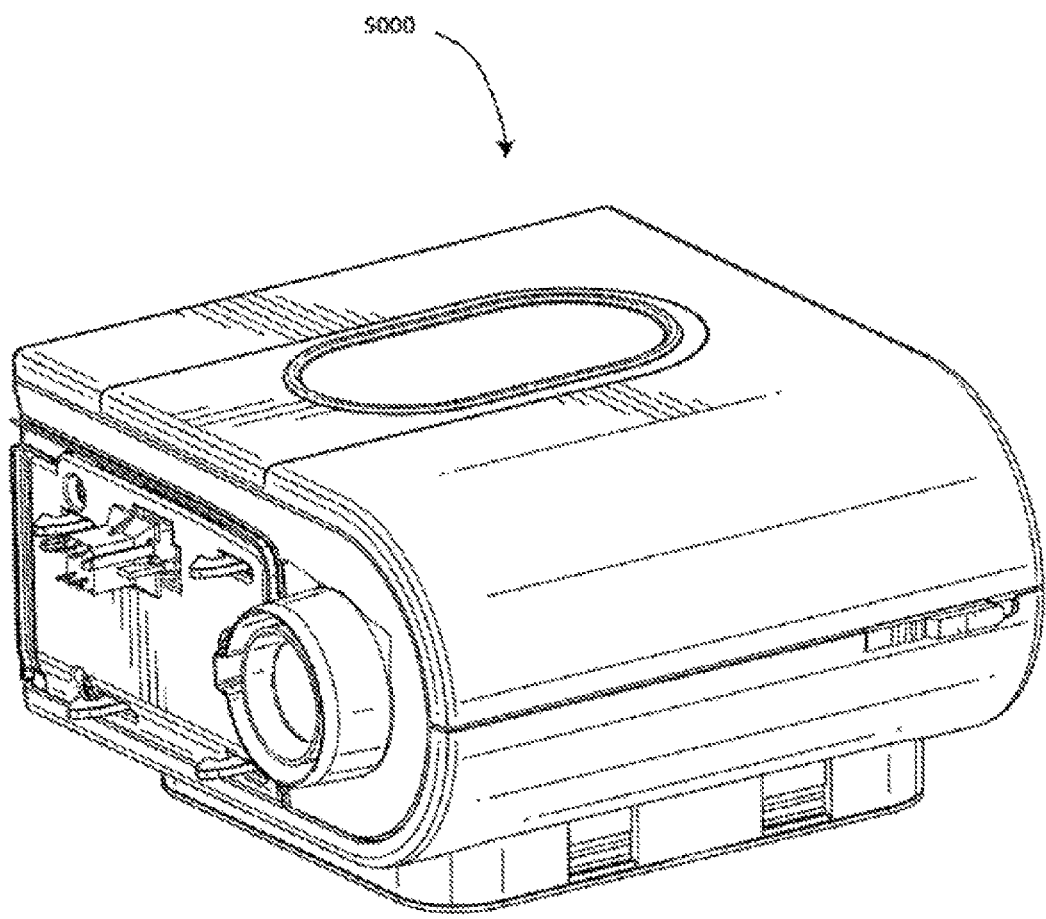

FIG. 5A shows a humidifier in accordance with one aspect of the present technology.

Figure 5B:
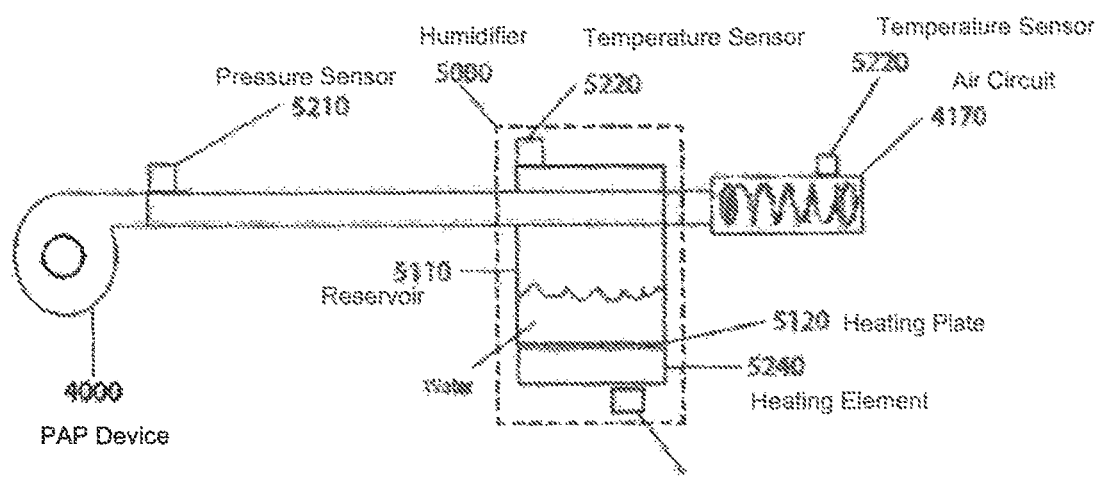

FIG. 5B shows a schematic of a humidifier in accordance with one aspect of the present technology.

Figure 5C:
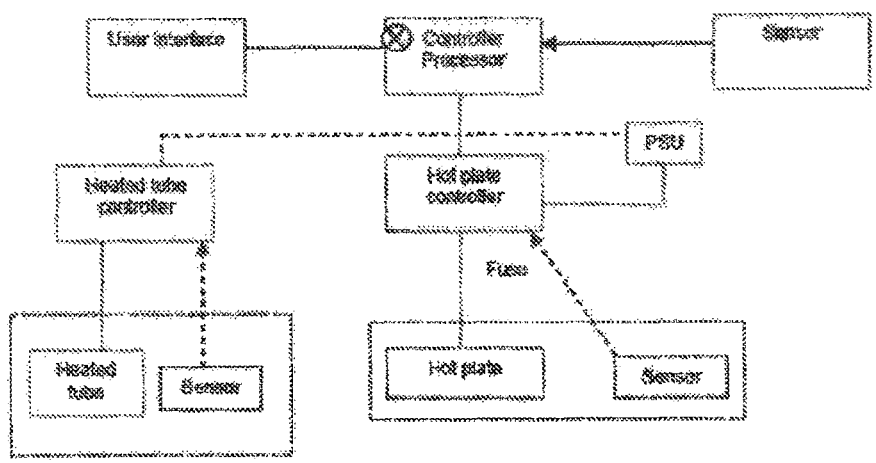

FIG. 5C shows a schematic diagram of a humidifier control circuit according to one aspect of the present technology

4.6 Breathing Waveforms

Figure 6A:
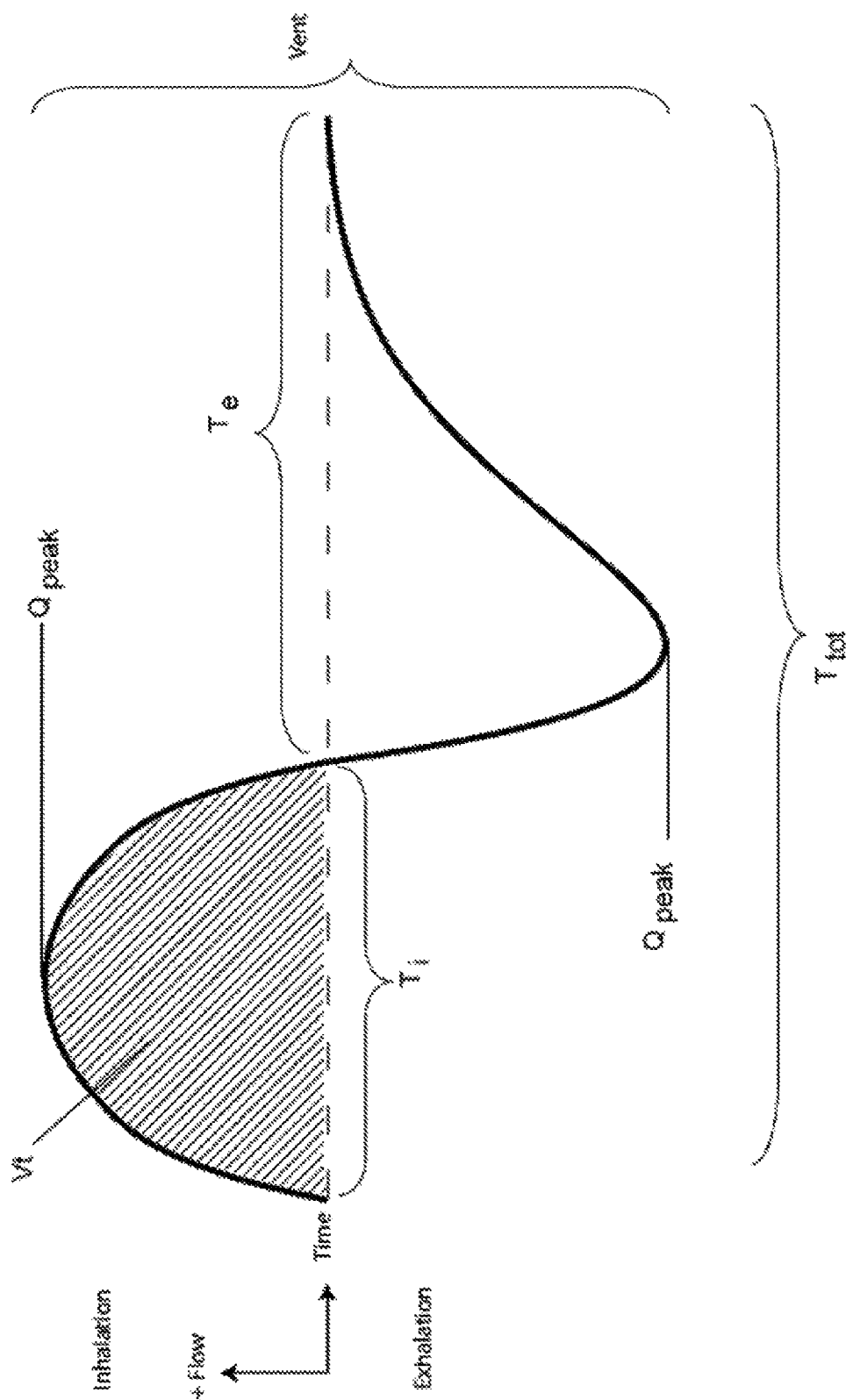

FIG. 6A shows a model typical breath waveform of a person while sleeping. The horizontal axis is time, and the vertical axis is respiratory flow.

Figure 7A:
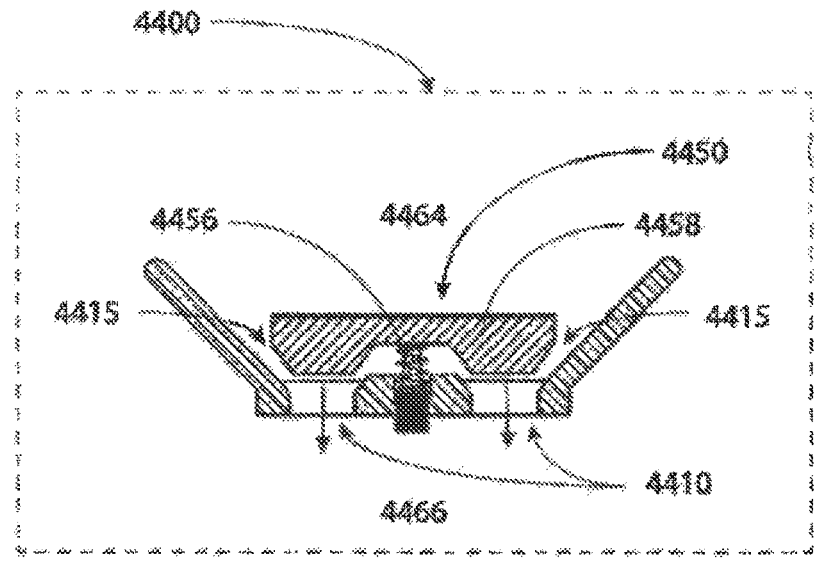

FIG. 7A shows an example of a servo-controlled vent valve, wherein the variable flow path is open to allow the exhaust of gas therethrough.

Figure 7B:
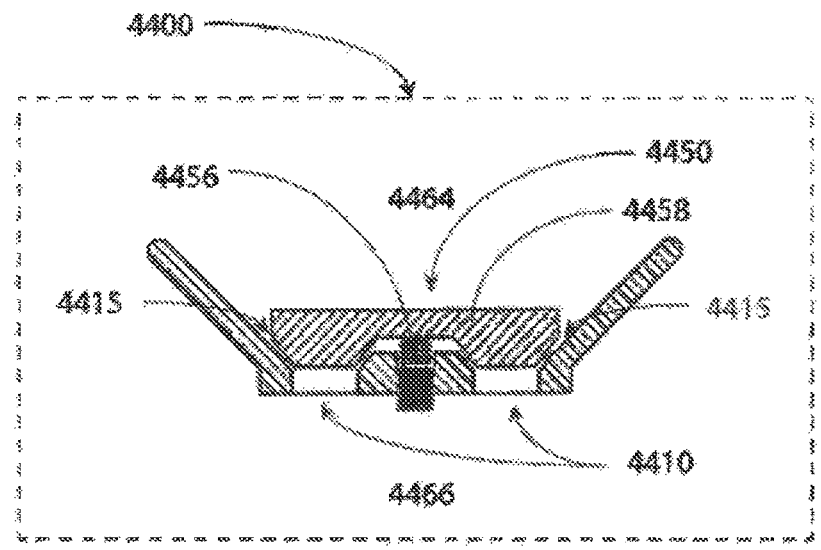

FIG. 7B shows an example of a servo-controlled vent valve, wherein the variable flow path is closed to prevent the exhaust of gas therethrough.

Figure 8A:
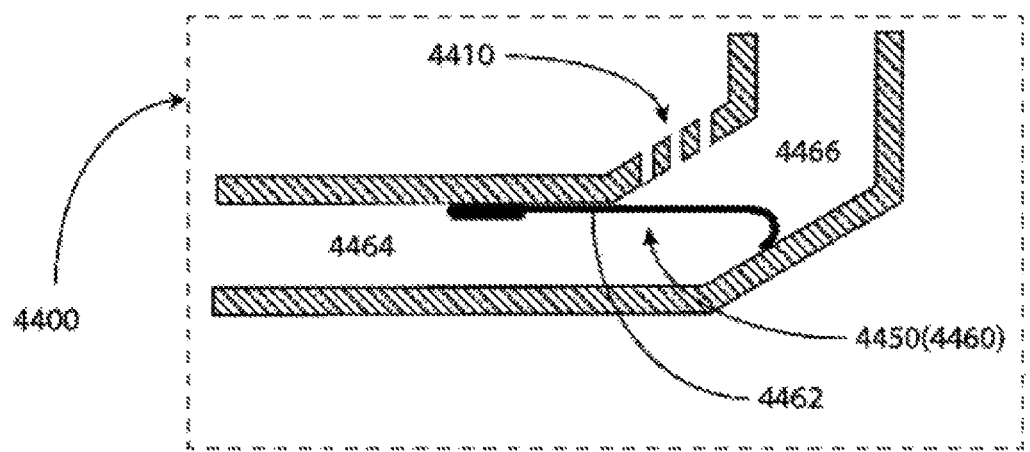

FIG. 8A shows an example of a flexible divider vent valve comprising a movable membrane, wherein the movable membrane is in a first position.

Figure 8B:
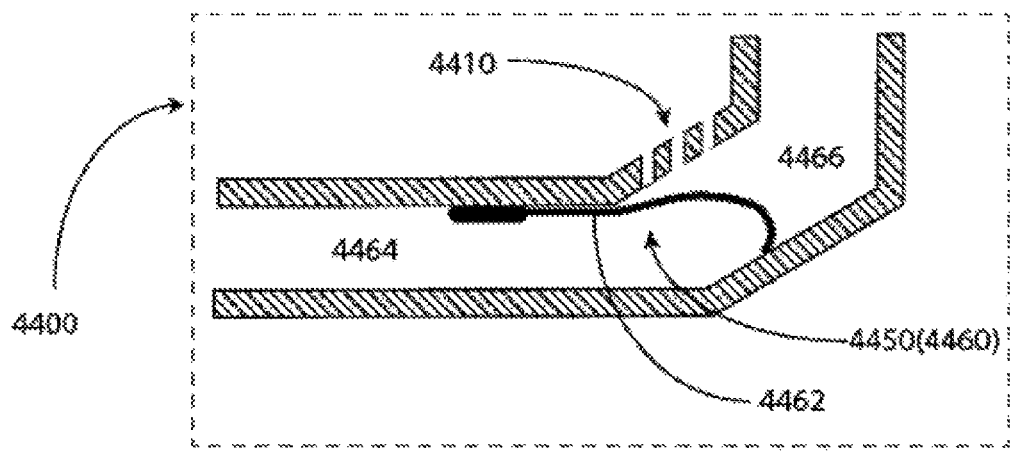

FIG. 8B shows an example of a flexible divider vent valve comprising a movable membrane, wherein the movable membrane is in a second position.

Figure 8C:
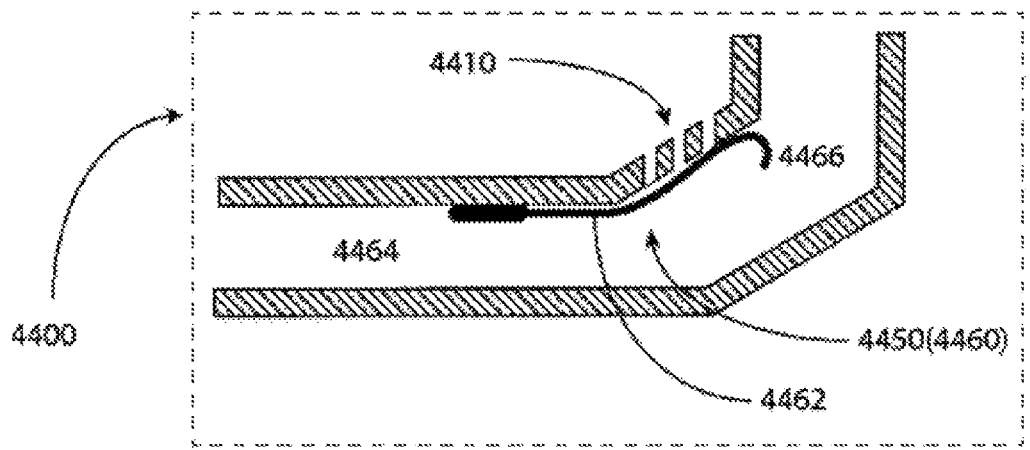

FIG. 8C shows an example of a flexible divider vent valve comprising a movable membrane, wherein the movable membrane is in a third position.

Figure 9:
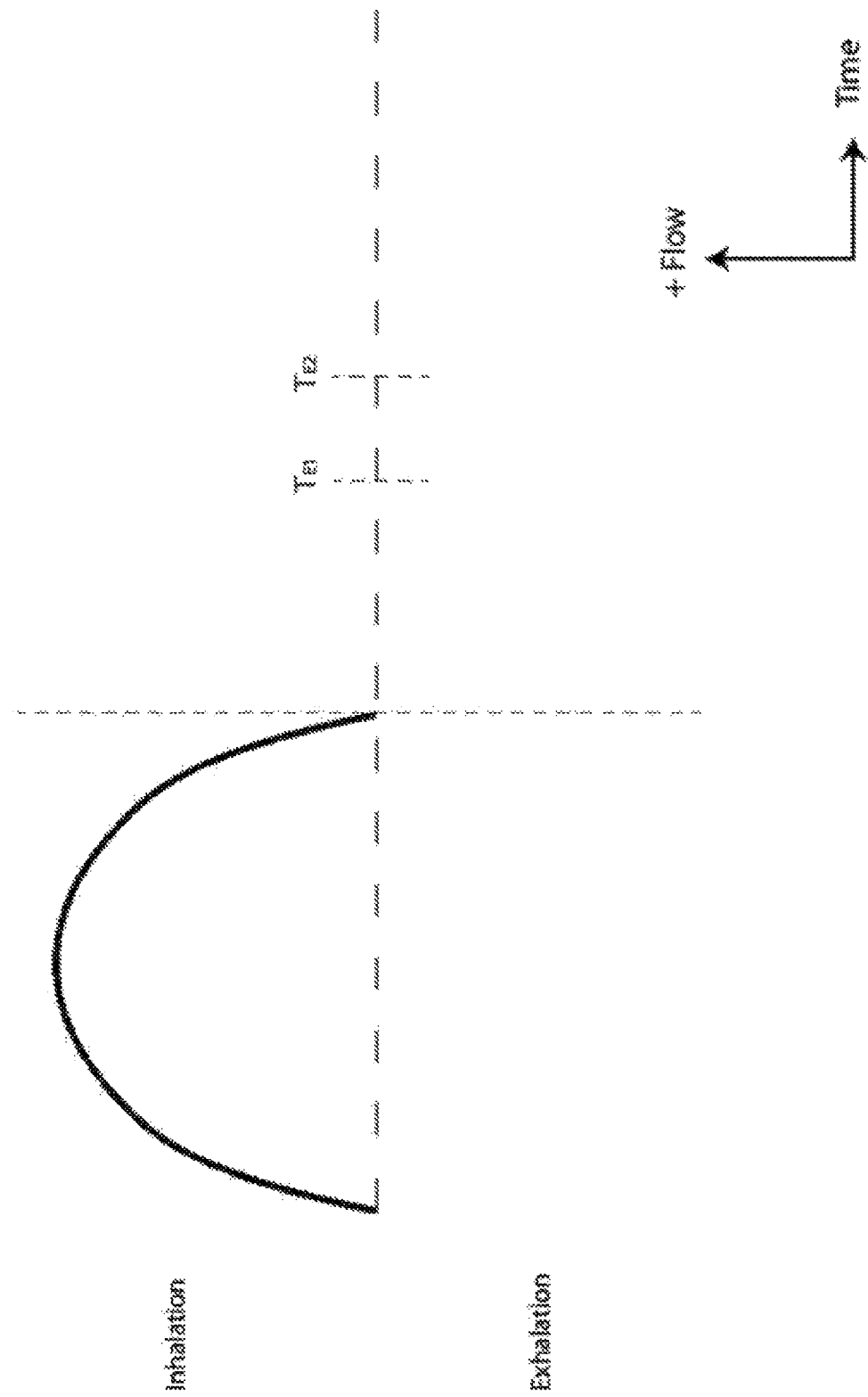

FIG. 9 shows an example of a breath flow waveform, wherein a measure of the respiratory flow is not available during the expiratory portion of the breath cycle.

Figure 10:
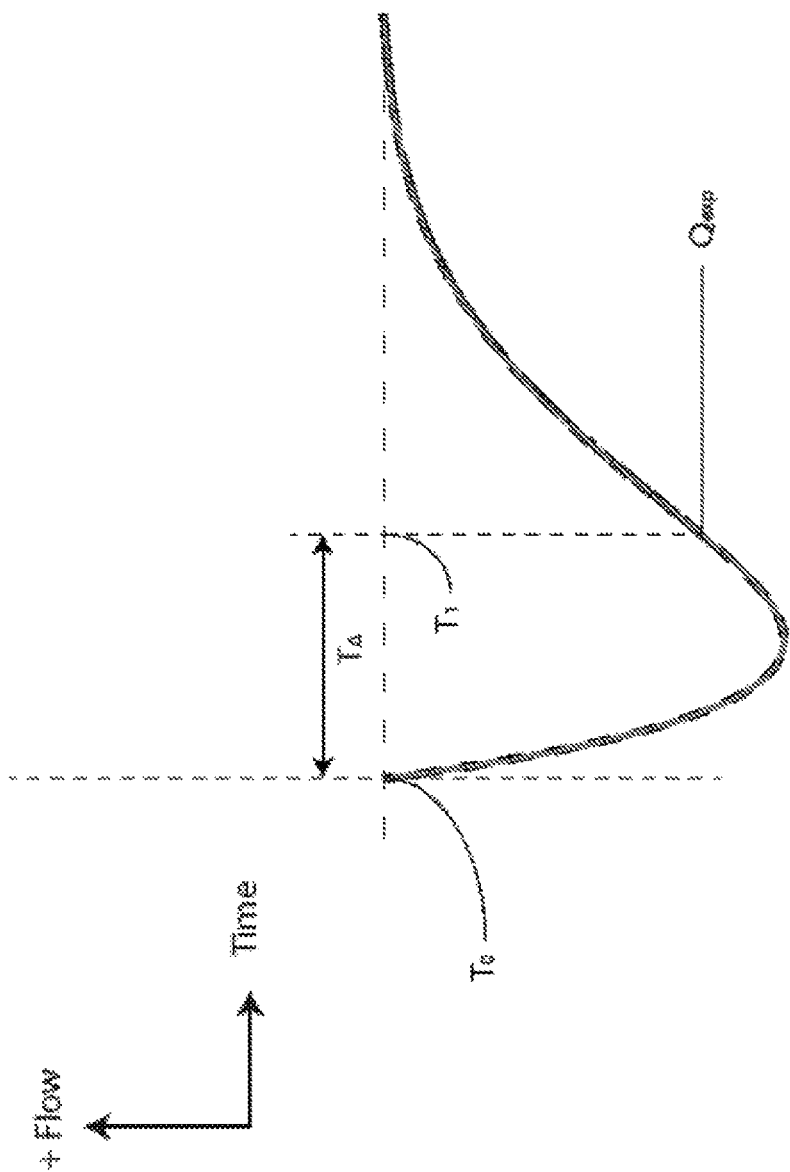

FIG. 10 shows an example of a model of an expiratory portion of a breath flow waveform.

Figure 11:
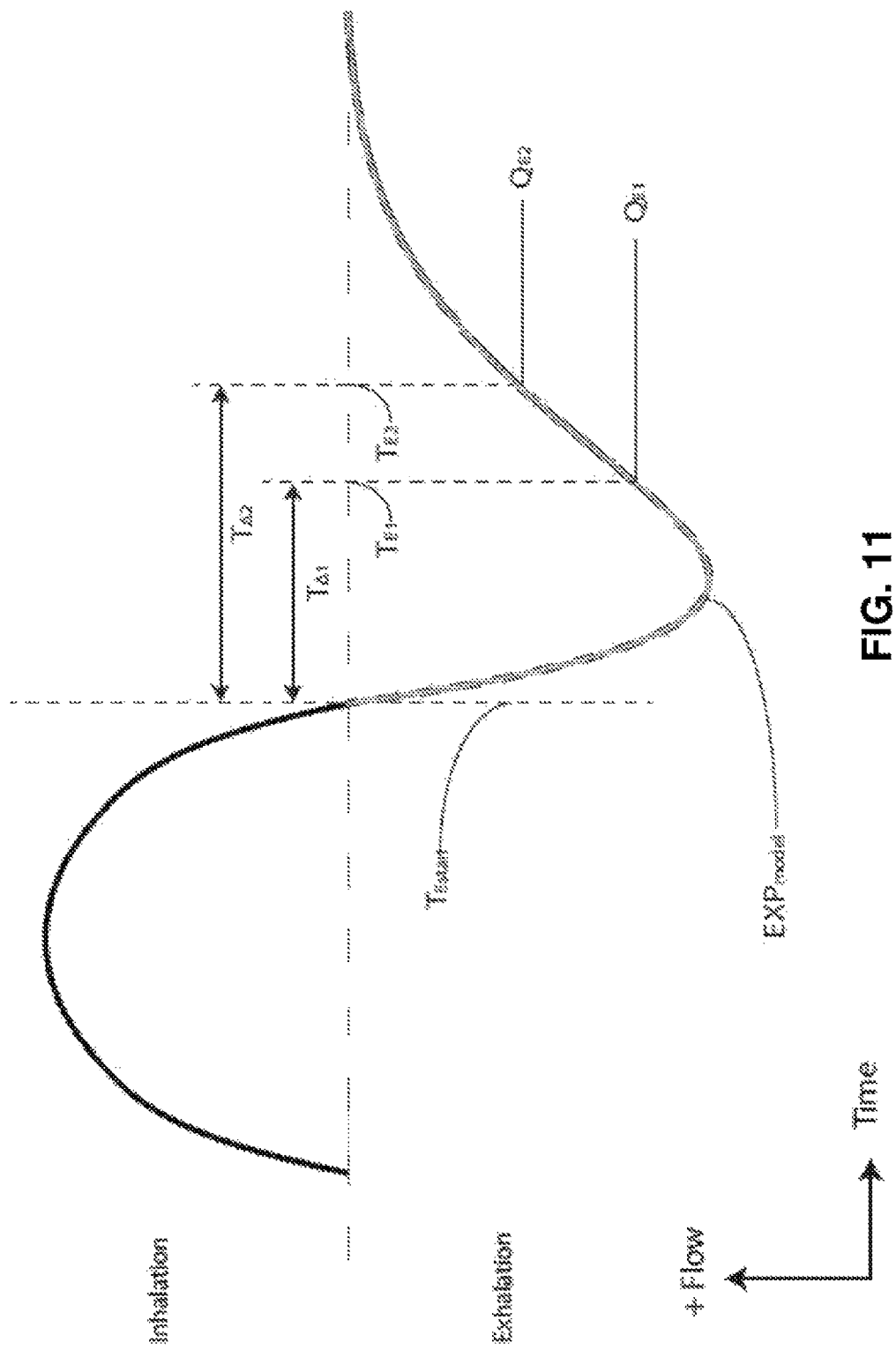

FIG. 11 shows an example of a breath flow waveform, wherein an inspiratory portion of the breath cycle is measured and an expiratory portion of the breath cycle is determined by a model.

Figure 11A:
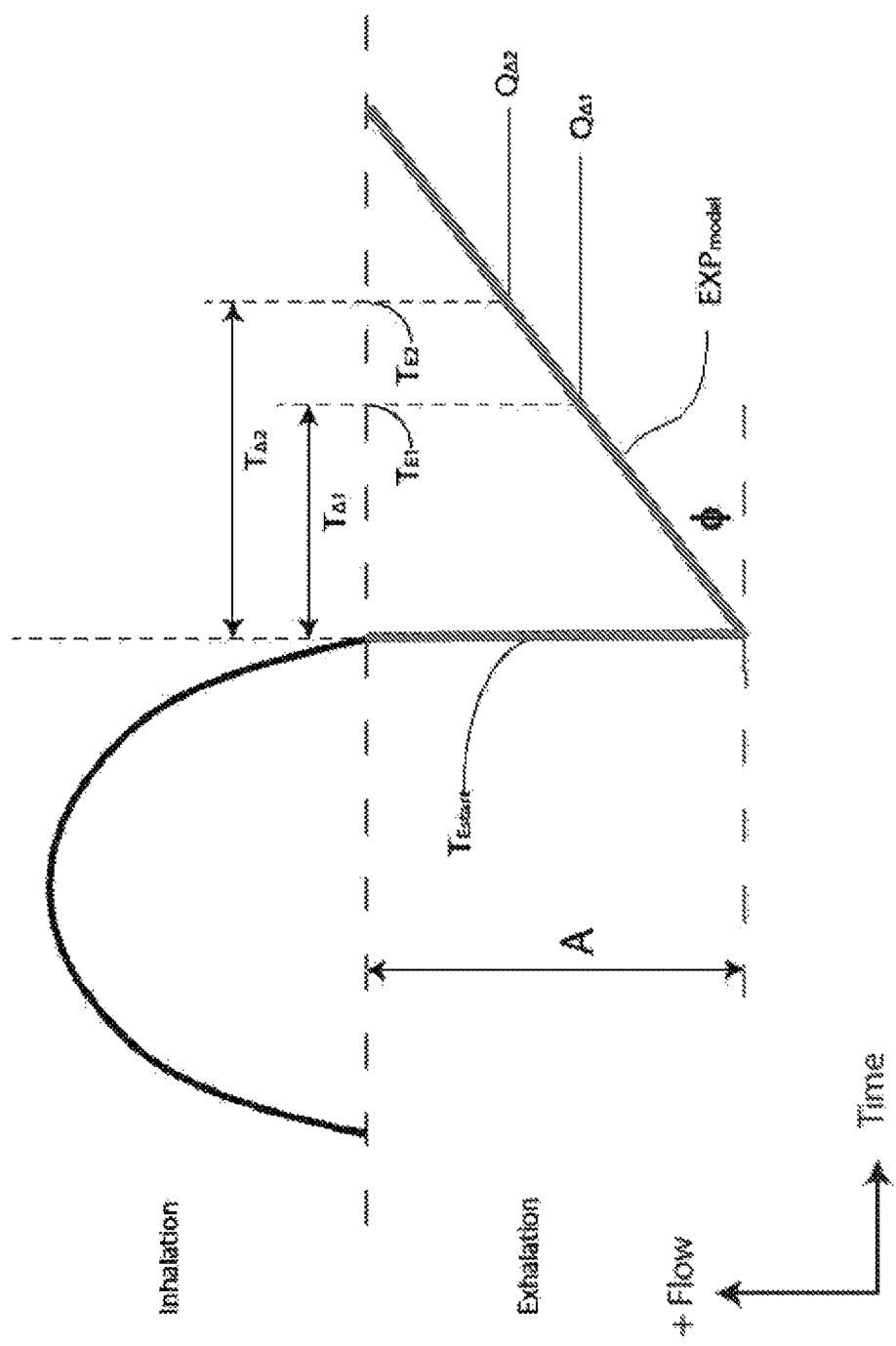

FIG. 11A shows another example of a breath flow waveform, wherein an inspiratory portion of the breath cycle is measured and an expiratory portion of the breath cycle is determined by a model.

Figure 11B:
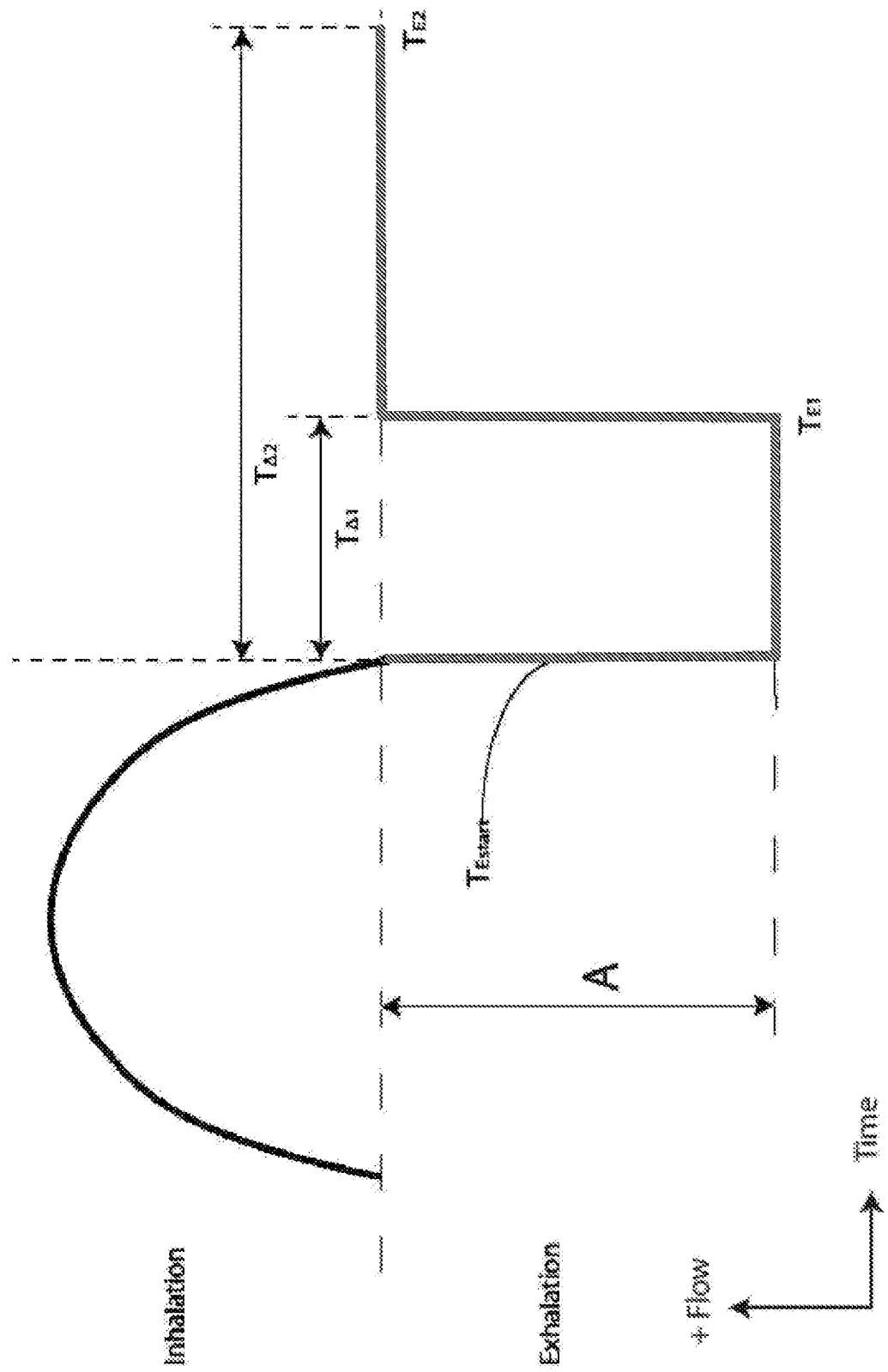

FIG. 11B shows a further example of a breath flow waveform, wherein an inspiratory portion of the breath cycle is measured and an expiratory portion of the breath cycle is determined by a model.

Figure 12B:
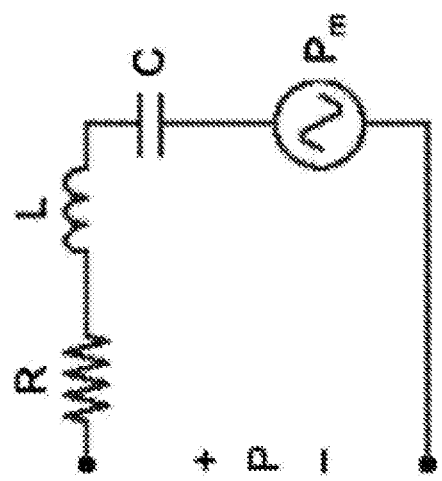
Figure 12A:
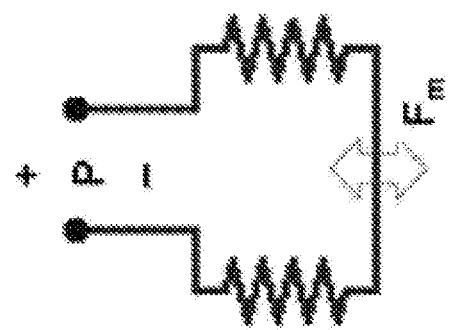

FIG. 12A shows a model of a lung represented as a mechanical model.

FIG. 12B shows a model of a lung represented as an electrical circuit.

Figure 13:
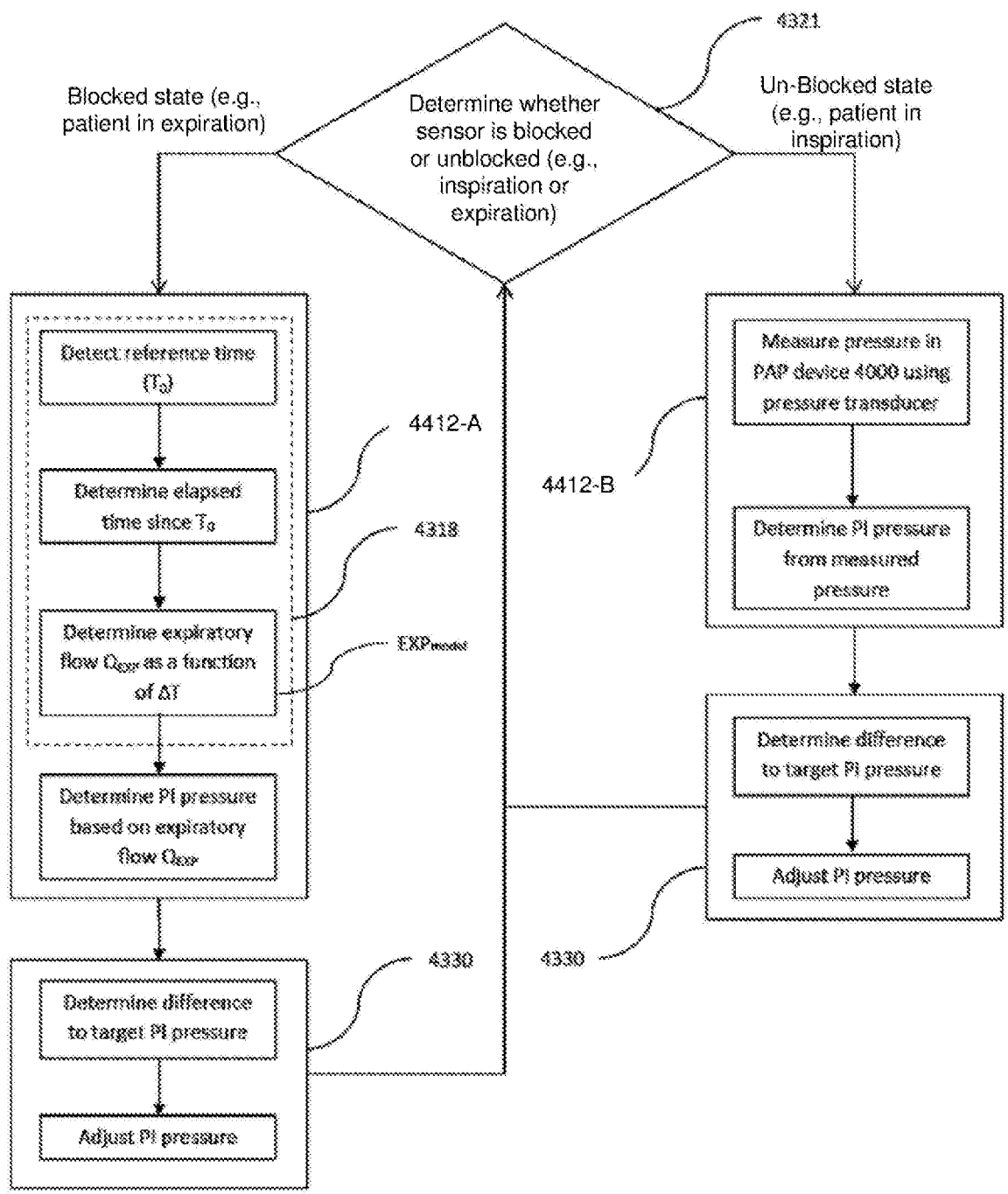

FIG. 13 shows a flow chart representation of one aspect of the present technology with a process for implementing control of a therapy apparatus with a sensor subjected to periodic blocking and unblocking.

Figure 14A:
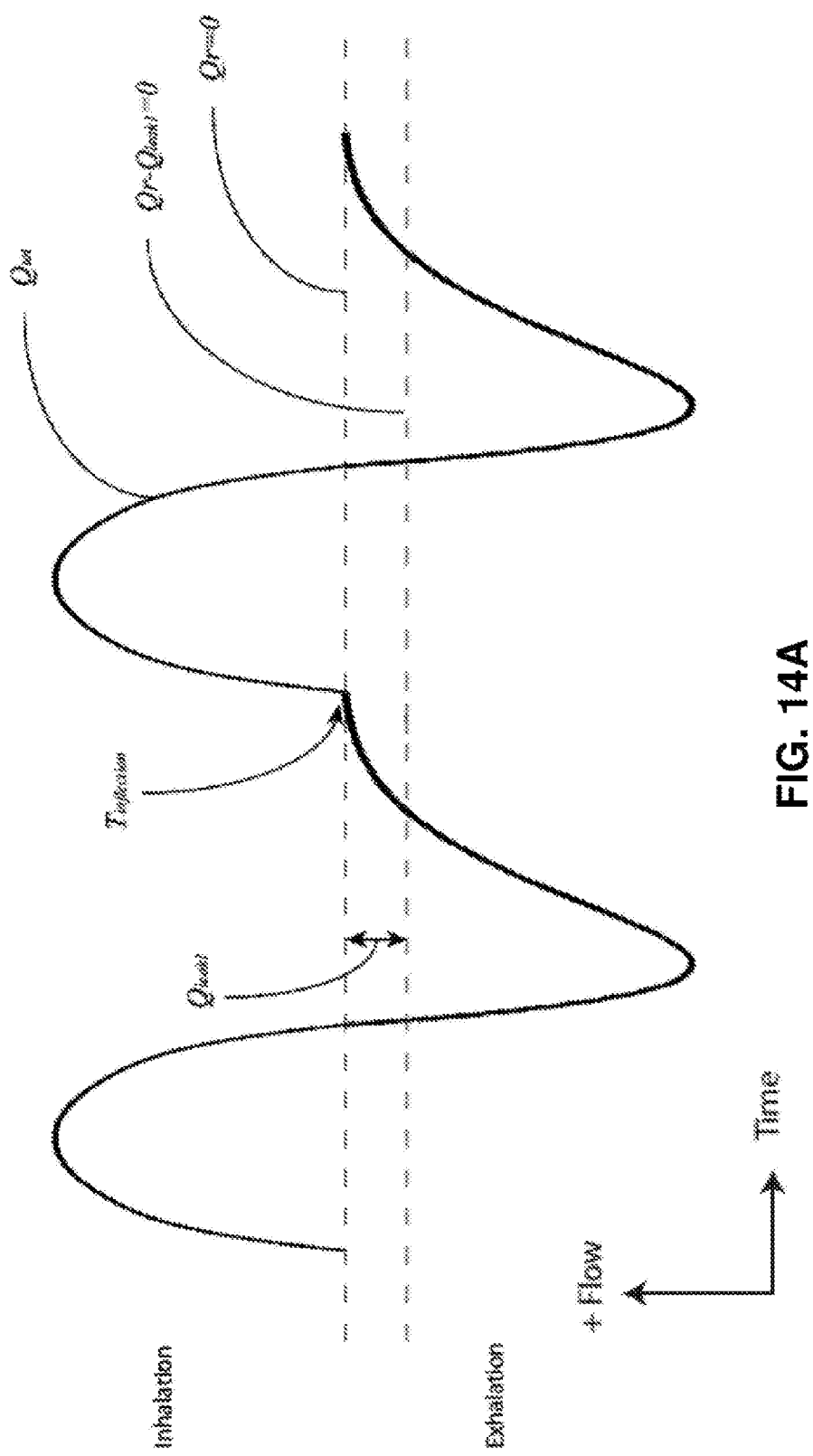

FIG. 14A shows a longer form of a model typical breath waveform as shown in FIG. 6A.

Figure 14B:
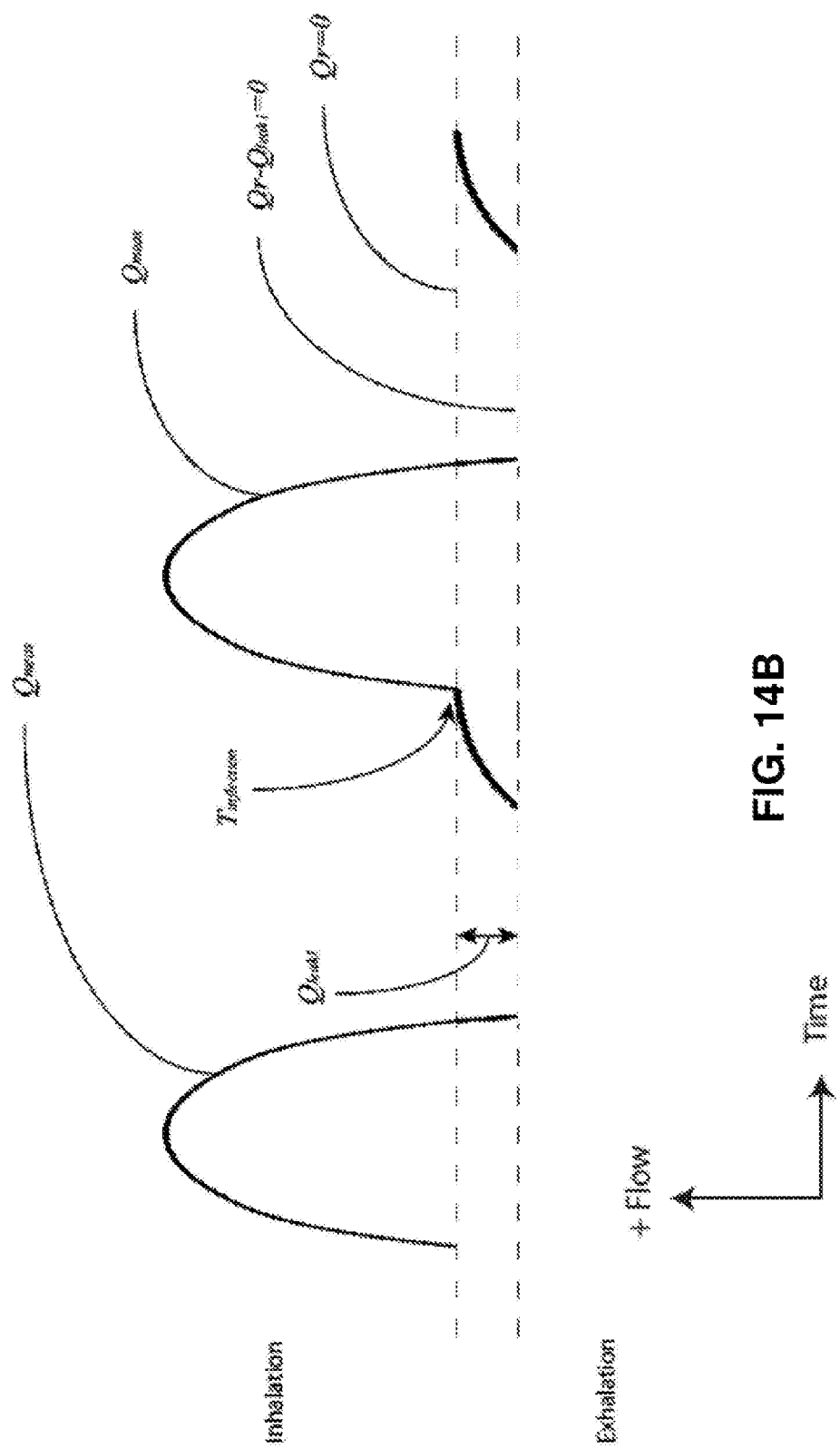

FIG. 14B shows a longer form of a model typical breath waveform as shown in FIG. 6A, wherein fluid communication between the flow sensor and the patient interface is blocked during expiration.

Figure 15:
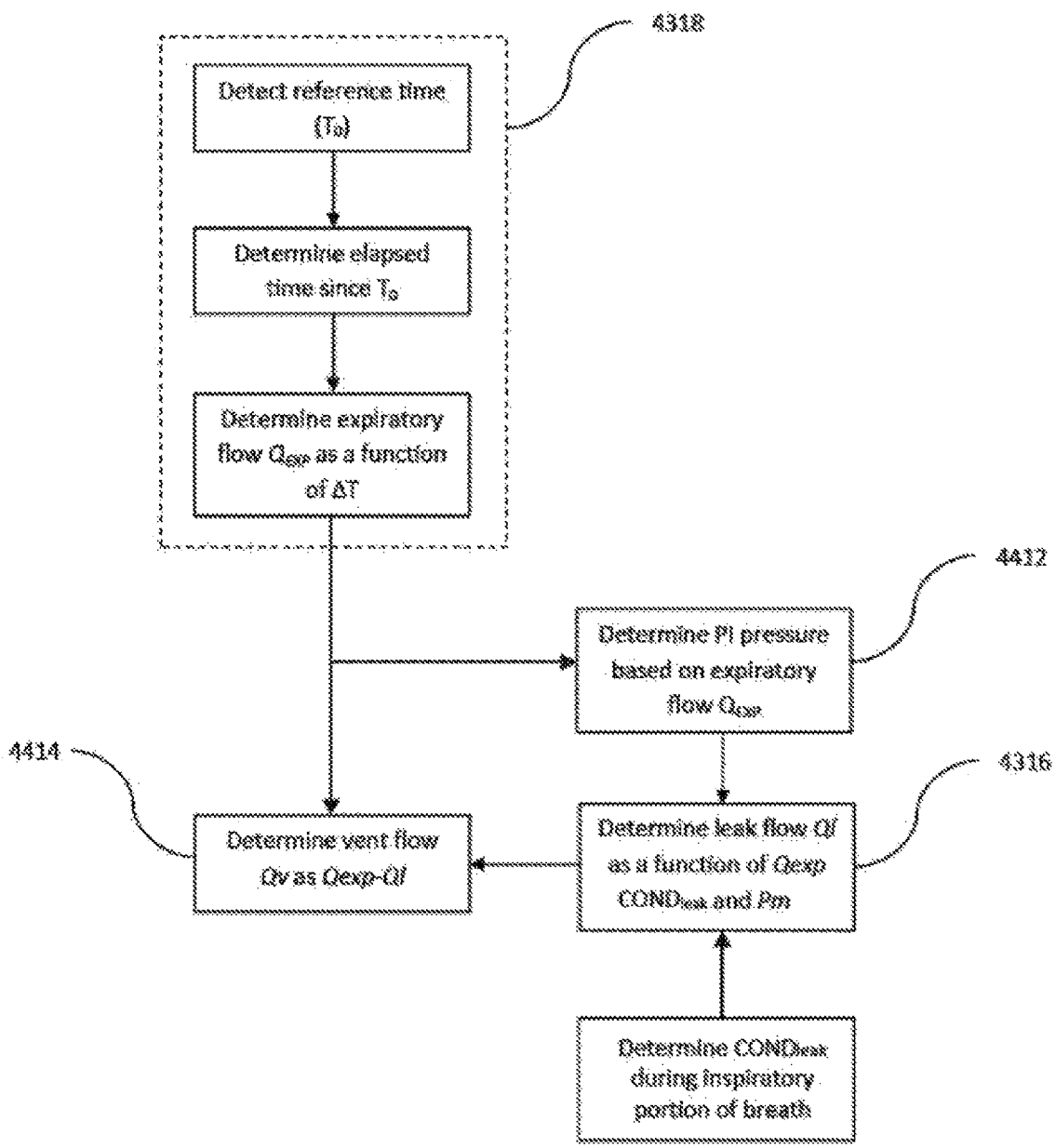

FIG. 15 shows a flow chart representation of one aspect of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

Aspects described in the present disclosure may be applicable for medical devices such as a PAP device, but also other types of respiratory devices not described in the present document. For example, aspects of the present technology may be applicable in respiratory devices where a flow of air is provided to a user. More specifically, aspects of the present technology may be applicable where the flow of air is provided to the user at a positive pressure relative to atmospheric pressures.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

In certain embodiments of the present technology, a supply of air at positive pressure is provided to the nasal passages of the patient via one or both nares.

5.3 Patient Interface 3000

A non-invasive patient interface 3000 in accordance with one aspect of the present technology comprises the following functional aspects: a seal-forming structure 3100, a plenum chamber 3200, a positioning and stabilising structure 3300 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

Figure 1A:
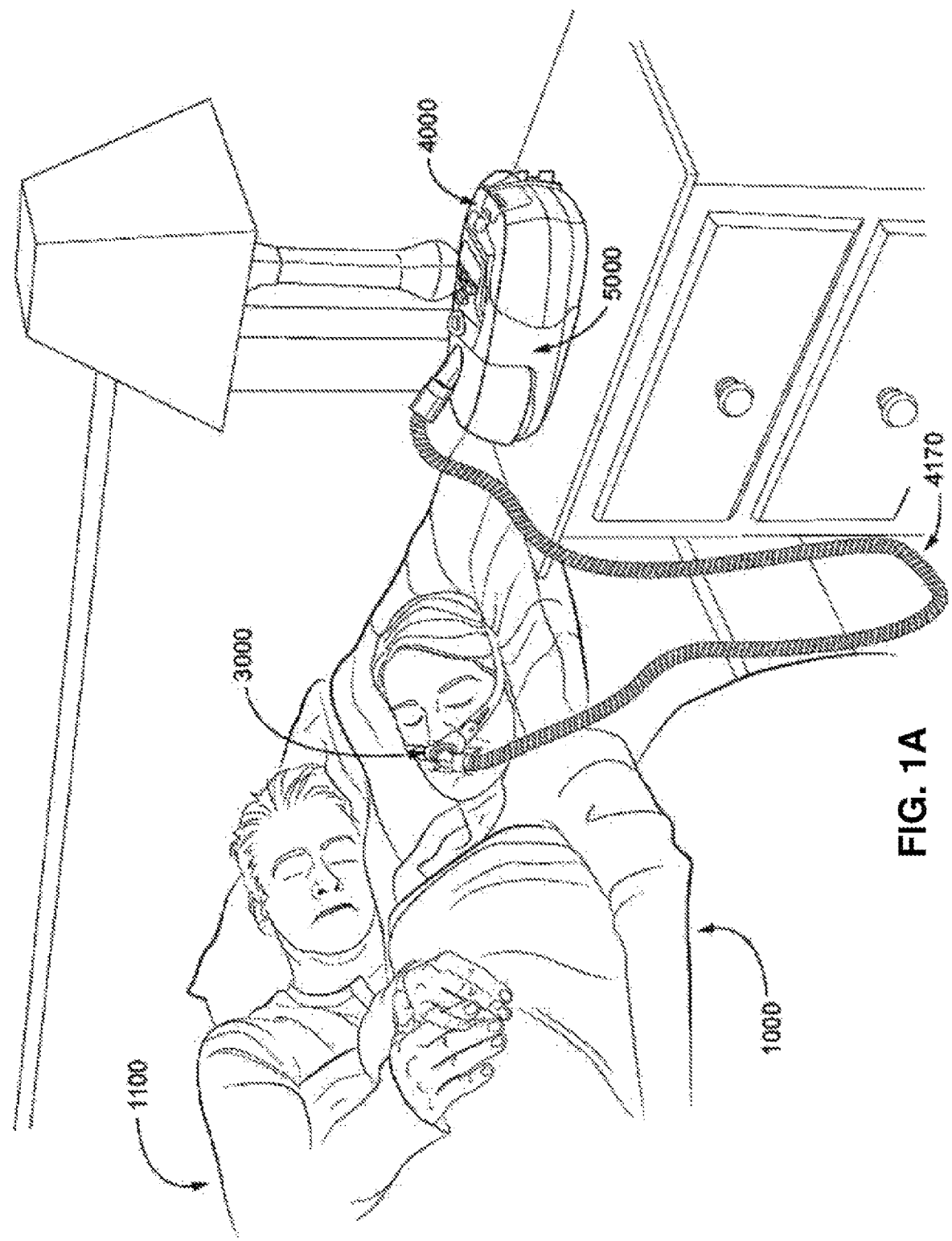
FIG. 1B shows an example PAP device 4000 coupled to a humidifier 5000 in use on a patient 1000 with patient interface 3000 in the form of a nasal mask.
FIG. 1C shows an example PAP device 4000 coupled to a humidifier 5000 in use on a patient 1000 with a patient interface 3000 in the form of full-face mask.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient (see FIG. 1a).

Figure 1B:
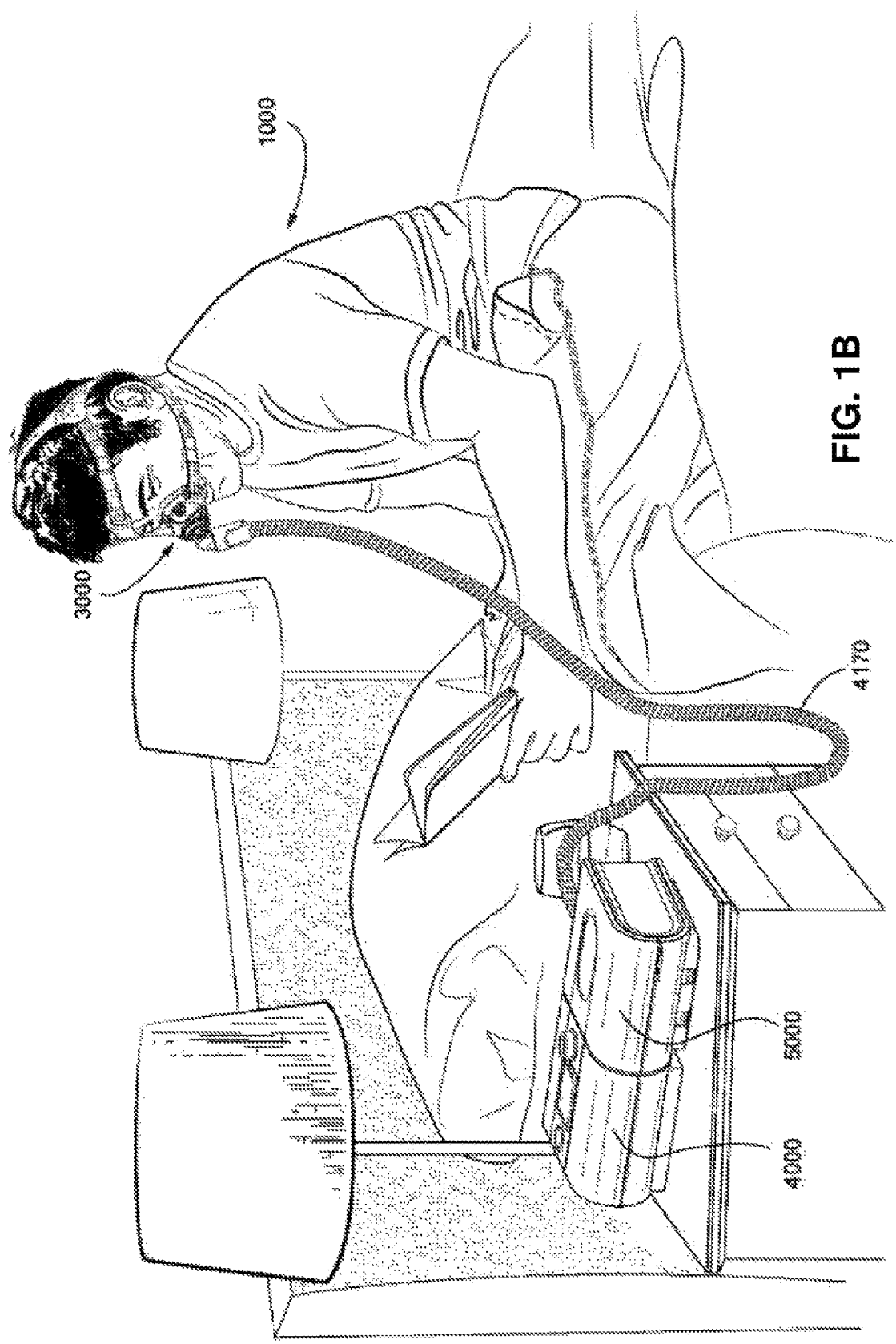

In one form the non-invasive patient interface 3000 comprises a seal-forming portion that forms a seal in use on an upper lip region (that is, the lip superior) of the patient's face (see FIG. 1b).

Figure 1C:

In one form the non-invasive patient interface 3000 comprises a seal-forming portion that forms a seal in use on a chin-region of the patient's face (see FIG. 1c).

5.3.2 Continuous Vent 3400

In one form, the patient interface 3000 include a continuous vent 3400 constructed and arranged to allow for the washout of exhaled carbon dioxide. To achieve washout of exhaled carbon dioxide, the continuous vent 3400 may be configured to exhaust a flow of exhaust gas from the patient interface.

One form of continuous vent 3400 in accordance with the present technology comprises a plurality of holes, for example, about 20 to about 80 holes, or about 40 to about 60 holes, or about 45 to about 55 holes.

According to some arrangements, the continuous vent 3400 may be located in the plenum chamber 3200, or in a decoupling structure 3500, e.g. a swivel 3510. In some cases, the continuous vent may be fixed, such as to have a fixed set of holes for venting, although in other cases, the continuous vent may be variably continuous to comprise variable venting characteristics while continuously exhausting a flow of exhaust gas from the patient interface.

5.3.3 Decoupling Structure(s) 3500

In one form the patient interface 3000 includes at least one decoupling structure 3500, for example a swivel or a ball and socket.

5.34 Connection Port 3600

Connection port 3600 allows for connection to the air circuit 4170.

5.3.5 Forehead Support 3700

In one form, the patient interface 3000 includes a forehead support 3700.

5.3.6 Anti-Asphyxia

In one form, the patient interface 3000 includes an anti-asphyxia valve.

5.3.7 Ports

In one form of the present technology, a patient interface 3000 includes one or more ports (not shown), that allow access to the volume within the plenum chamber 3200. In one form this allows a clinician to supply supplemental oxygen. In one form this allows for the direct measurement of a property of gases within the plenum chamber 3200, such as the pressure.

5.4 Air Circuit 4170

An air circuit 4170 in accordance with an aspect of the present technology is constructed and arranged to allow a flow of air or breathable gases between various components, such as between the pneumatic block 4020 and the patient interface 3000. In one arrangement, a first air circuit 4170 may extend between an outlet of the PAP device 4000 and an inlet of the humidifier 5000, and a second air circuit 4170 may extend between an outlet of humidifier 5000 and the patient interface 3000. In another arrangement the inlet of humidifier 5000 may be directly coupled to the outlet of the PAP device 4000 without the need for an intervening air circuit 4170. However, in such an arrangement an air circuit 4170 may be provided between the outlet of the humidifier 5000 and the patient interface 3000.

5.4.1 Variable Vent 4400

According to one form of the present technology, a respiratory treatment system (e.g. as a part of an air circuit 4170 or a connector) may comprise a variable vent 4400 configured to exhaust a flow of exhaust gas from the patient interface 3000. A variable vent 4400 may be located away from the patient interface while being in fluid communication with the patient interface 3000. Suitable locations for the variable vent 4400 may include in the air circuit 4170, in the PAP device 4000, or in a separate connector connected to the air circuit 4170 between the patient interface 3000 and the PAP device 4000. The variable vent 4400 may also be provided within the patient interface 3000 in a similar manner to and instead of, or in addition to, the continuous vent 3400 described above. In some cases, the volume of air path present, for example of the air circuit 4170, between the variable vent 4400 and the patient interface 3000 may affect how much of the exhaled air is re-breathed by the patient. The variable vent 4400 may be located nearer to the patient interface 3000 than to the PAP device 4000 or blower 4142 in order to reduce any re-breathing of $CO_2$ by the patient. Such a variable vent may, for example, be a vent assembly described in U.S. Patent Application Publication No.

US-2014-0283831-A1, the entire disclosure of which is incorporated herein by reference.

5.4.2 Vent Valve 4450

In one form, the variable vent 4400 may comprise a vent valve 4450 to overcome some of the disadvantages associated with use of a continuous vent 3400. As described above, some of the known disadvantages associated with use of a continuous vent may include increased loss of humidity, lowered energy efficiency, increased noise output and lowered maximum therapy pressure level. These disadvantages may be more significant during an expiration phase of a patient's breath.

A vent valve 4450 may overcome the above disadvantages by selectively blocking fluid communication between components as required. Preferably, the vent valve 4450 may block fluid communication between the patient interface 3000 and the variable vent 4400 during inspiration, and allow fluid communication between the patient interface 3000 and the variable vent 4400 during expiration. The vent valve 4450 may also allow fluid communication between the blower 4142 and the patient interface 3000 during inspiration, and block fluid communication between the blower 4142 and the patient interface 3000 during expiration.

In some cases, the vent valve 4450 may be configured to simultaneously block, or simultaneously allow, fluid communication between two sets of components. For instance, the vent valve 4450 may be configured to simultaneously block, or simultaneously allow, fluid communication between the patient interface 3000 and the variable vent 4400 as well as fluid communication between the patient interface 3000 and the blower 4142. Alternatively, or additionally, the vent valve 4450 may be configured so that at any one time, it blocks fluid communication between one set of components and allows fluid communication between another set of components. For instance, the vent valve 4450 may be configured to block fluid communication between the patient interface 3300 and the blower 4142 while allowing fluid communication between the patient interface 3000 and the variable vent 4400.

It should be understood that in some arrangements, the vent valve 4450 may not completely block fluid communication between two components. Many of the advantages described above in relation to using a vent valve 4450 may be achieved, for example, by reducing the amount of gas flow between components, without completely blocking fluid communication therebetween. It should be also understood that, although according to some arrangements the vent valve 4450 selectively blocks fluid communication between components based on indicators such as an expiratory characteristic or a model of a respiratory circuits, the vent valve 4450 may also selectively block fluid communication between components based on other indicators. One suitable indicator may be the presence of Cheyne-Stokes Respiration, a treatment for which may be use of a vent valve 4450 to increase the amount of $CO_2$ that is rebreathed by the patient.

As described above, a vent valve 4450 may be able to selectively block fluid communication between components such as the blower 4142, the patient interface 3000 and the variable vent 4400. Accordingly, at least some portion of the vent valve 4450 may be located closer to the patient interface 3000 than the blower 4142 in order to selectively block fluid communication between the variable vent 4400 and other components.

The vent valve 4450 may be constructed in one or more of multiple forms suitable to provide a variable venting function. One suitable form of the vent valve 4450 may use a servo-controlled vent valve, for example as shown in FIGS. 7a-7b or as disclosed in co-owned PCT application publication number WO 2013/040198. Another suitable form may use a flexible divider vent valve 4460, for example as shown in FIG. 8a~8h or as disclosed in co-owned PCT application publication number WO 2013/067592, The entire contents of both PCT patent applications WO 2013/040198 and WO 2013/067592 are incorporated herein in their entirety by cross-reference.

In some arrangements of the present technology, the use of a vent valve 4450 may affect the way in which a pressure in the patient interface 3000 (i.e., gas pressure) is adjusted. In some prior systems, the pressure in the patient interface 3000 is adjusted by controlling the operation of the blower 4142, such as by increasing or decreasing a rotational speed of the blower 4142 to increase or decrease a pressure in the patient interface respectively. When the blower 4142 is in fluid communication with the patient interface 3000, the pressure in the patient interface 3000 may be correlated to the pressure at the outlet of the blower 4142. The correlation may be characterised as a pressure drop, which may be dependent on a number of factors such as blower speed, length and profile of the air circuit 4170, or characteristics of the patient interface including size of the plenum chamber 3200 or arrangement of the variable vent 4400.

An adjustment of the pressure in the patient interface 3000 may affect the pressure of the flow of breathable gas at another location or component which is in fluid communication with the patient interface 3000. As a corollary, it would be understood that instead of aiming to adjust the pressure in the patient interface 3000, pressure at another location or component such as the pressure in the air circuit 4170 may be used as an adjustable target pressure while taking advantage of the present technology.

It is noted that aspects of the present technology in relation to adjustments of pressure and/or change of flow impedance may be suitable for medical devices and other types of respiratory devices, such as those wherein an air flow is provided to a user at a positive pressure. For example, an ability of a respiratory device to control a pressure delivered to its user may improve comfort of the user, which may provide usability benefits.

One known prior method of determining pressure in the patient interface 3000 is to measure a pressure near the outlet of the blower 4142 and to apply a pressure drop correction to compensate for loss in pressure as air flows therethrough. The ability to determine the pressure in the patient interface 3000 has been used to compensate for any changes caused by the patient's inspiration or expiration. Typically, inspiration may decrease the pressure in the patient interface 3000 and expiration may increase the pressure in the patient interface 3000. Some prior devices have regulated pressure in the patient interface 3000 during inspiration and during expiration by measuring a change in pressure, and changing the speed of the blower 4142 accordingly.

In the present technology, various methods may be used to adjust a pressure in the patient interface 3000, for example through a variable property of a vent valve 4450. In one form, flow impedance of the vent valve 4450 may be changed to adjust pressure in the patient interface 3000. In the case of the vent valve 4450 taking the form of a servo-controlled vent valve as shown in FIG. 7A and FIG. 7B, its flow impedance may be changed by varying the opening of an exhaust area 4410 of the variable vent 4400 to vary the amount of venting through the variable vent 4400. One suitable form of varying the opening of a variable flow path 4415 to the exhaust area 4410 of the variable vent 4400 is shown in FIG. 7A and FIG. 7B, where an actuator 4456 moves a movable portion, such as a valve body 4458, to adjust the level of opening of the variable flow path 4415 to the exhaust area 4410 of the variable vent 4400. FIG. 7A shows an example where the variable flow path 4415 to the exhaust area 4410 of the variable vent 4400 is at least partially open to allow the exhaust of gas as indicated by the arrows. FIG. 7B shows an example wherein the variable flow path 4415 to the exhaust area 4410 of the variable vent 4400 is substantially dosed by positioning the valve body 4458 is a substantially closed or blocked position. In some arrangements, the variable vent 4400 may be configured to block fluid communication entirely between a first side 4464 and a second opposing side 4466.

Alternatively, in one form as shown in FIG. 8A and FIG. 8B, the flexible divider vent valve 4460 may comprise a movable portion, such as a membrane 4462. In some cases, the membrane 4462 may be deformable. The movement and/or deflection of the membrane 4462 may affect the flow impedance through the exhaust area 4410 and/or between the first side 4464 and a second side 4466 of the membrane 4462. The membrane 4462 may be configured (e.g. deflected and/or re-positioned) by changing a pressure difference between a first side 4464 of the membrane 4462 and a second opposing side 4466 of the membrane 4462, thereby having a resulting force act on the membrane. In some arrangements, the blower 4142 may be used to change a pressure on the first side 4464 of the membrane 4462 thereby changing the net pressure applied thereto (between the first side 4464 and the second side 4466) and thus re-configuring the membrane. FIG. 8B shows an example wherein the membrane 4462 is arranged so that the impedance of the variable vent 4400 is higher than in the configuration shown in FIG. 8A. This is caused by a greater increase in the pressure on the first side 4464 of the membrane than the pressure on the second side 4466 of the membrane resulting in the deflection of the membrane towards the second side 4466. In contrast the impedance of the variable vent 4400 as shown in FIG. 8A may be substantially balanced between the first side 4464 and the second side 4466 of the membrane, resulting in a lower impedance configuration of the variable vent 4400. Either, or both, of the configurations shown in FIG. 8A or 8B (or any configurations therebetween) may be desired during an expiration phase of the respiratory cycle to allow expired gas to be exhausted through the exhaust area 4410. For example, the configuration shown in FIG. 8A may be desired where the expiratory flow rate is relatively high, whereas the configuration shown in FIG. 8B may be desired when the expiratory flow has subsequently decreased. The pressure of the variable vent 4400 may be increased on the first side 4464 of the membrane to further deflect the membrane to at least partially or completely block the exhaust area 4410 and consequently open up the path between the first side 4464 and the second side 4466 of the variable vent 4400 as shown in FIG. 8C. Such an arrangement may be desired during an inspiration phase of the respiratory cycle.

According to one aspect of the vent valve 4450, the blower 4142 may not be in fluid communication with the patient interface 3000 during some portions of therapy, such as during expiration. In this arrangement, a pressure measured near the outlet of the blower 4142 may not have sufficient correlation to a pressure in the patient interface 3000 in order to determine the pressure in the patient interface 3000.

In some instances, it may be possible to measure a gas property, such as pressure or flow rate in the patient interface 3000 side of the vent valve 4450. This may be achieved by introduction of a sensor on the patient interface 3000 side of the vent valve 4450, or by introduction of a fluid communication such as a sensing lumen or a pressure port between the two sides of the vent valve 4450. However, the introduction of a sensor may add cost to manufacturing and/or add complexities in order for a controller 4230 to communicate with a sensor located away from the blower 4142. Introduction of a pressure port or a sensing lumen may also introduce additional complexities and cost. In some cases, introduction of a pressure port or a sensing lumen may also increase $CO_2$ re-breathing as at least some of the exhaust gas may be stored in the pressure port/sensing lumen, which may be also undesirable. Still further, introduction of such additional components and/or complexities may adversely affect robustness of the system, or make it more onerous to achieve the equivalent level of robustness.

According to one aspect of the present technology, an expiratory characteristic may be determined while the vent valve 4450 blocks fluid communication between components, such as between the blower 4142 and the patient interface 3000. In some cases, the expiratory characteristic may be determined without a measurement of a gas property on the patient interface 3000 side of the vent valve 4450 while fluid communication is blocked thereto. For instance, a model of the patient's respiratory circuit and various components connected to the patient's respiratory circuit may be used to determine an expiratory characteristic such as the expiratory flow from the patient's lungs. The expiratory characteristic may then be used as an input parameter to a controller 4230, for example to adjust the pressure in the patient interface 3000.

Although in the above discussion of the variable vent 4400 a single vent valve 4450 is described to selectively block fluid communication between components such as the blower 4142, the patient interface 3000 and the variable vent 4400, it should be understood that multiple, discrete vent valves 4450 may be used to achieve the same effect. A person skilled in the art would also understand that in some cases, the vent valve 4450 may be displaced from the exhaust area 4410, while retaining benefits from the present technology.

Modelling methods to determine expiratory characteristics while the vent valve 4450 blocks communication between components, and use of the determined expiratory characteristic will be described in further detail below.

5.5 Pap Device 4000

A preferred PAP device 4000 in accordance with one aspect of the present technology comprises mechanical and pneumatic components 4100, electrical components 4200 and is programmed to execute one or more algorithms 4300. The PAP device preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124. One or more pressure sensors 4272 and flow sensors 4274 may be included in the pneumatic path.

The preferred pneumatic block 4020 comprises a portion of the pneumatic path that is located within the external housing 4010.

The PAP device 4000 preferably has an electrical power supply 4210, one or more input devices 4220, a central controller 4230, a therapy device controller 4240, a pressure device 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

The central controller 4230 of the PAP device 4000 is programmed to execute one or more algorithm modules 4300, preferably including a pre-processing module 4310, a therapy engine module 4320, a pressure control module 4330, and further preferably a fault condition module 4340.

5.5.1 PAP Device Mechanical & Pneumatic Components 4100

5.5.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

5.5.1.2 Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

5.5.1.3 Pressure Device 4140

In a preferred form of the present technology, a pressure device 4140 for producing a flow, or a supply, of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_3$O.

The pressure device 4140 is under the control of the therapy device controller 4240.

5.5.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

Transducers may be internal of the device, or external of the PAP device. Internal transducers may include for example pressure, flow, speed or oxygen sensors. External transducers may be located for example on or form part of the air delivery circuit, e.g. the patient interface. External transducers may be in the form of non-contact sensors such as a Doppler radar movement sensor that transmit or transfer data to the PAP device.

5.5.1.4.1 Flow 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the processor 4230.

5.5.1.4.2 Pressure 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the processor 4230. In one form, the signal from the pressure transducer 4272 is filtered prior to being received by the processor 4230.

5.5.1.4.3 Motor Speed 4276

In one form of the present technology a motor speed signal 4276 is generated. A motor speed signal 4276 is preferably provided by therapy device controller 4240. Motor speed may, for example, be generated by a speed sensor, such as a Hall effect sensor.

5.5.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.5.1.6 Oxygen Delivery 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

5.5.2 PAP Device Electrical Components 4200

5.5.2.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

5.5.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.5.2.3 Central Controller 4230

In one form of the present technology, the central controller 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARM9-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal(s) from one or more transducers 4270, and one or more input devices 4220.

The processor 4230 is configured to provide output signal(s) to one or more of an output device 4290, a therapy device controller 4240, a data communication interface 4280 and humidifier controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a PAP device 4000. However, in some forms of the present technology the processor(s) may be implemented discretely from the flow generation components of the PAP device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

5.5.2.4 Clock 4232

Preferably PAP device 4000 includes a clock 4232 that is connected to processor 4230.

5.5.2.5 Therapy Device Controller 4240

In one form of the present technology, therapy device controller 4240 is a pressure control module 4330 that forms part of the algorithms 4300 executed by the processor 4230.

In one form of the present technology, therapy device controller 4240 is a dedicated motor control integrated circuit. For example, in one form a MC33035 brushless DC motor controller, manufactured by ONSEMI is used.

5.5.2.6 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

5.5.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively. PAP device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.5.2.8 Data Communication Systems 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

5.5.2.9 Output Devices Including Optional Display, Alarms 4290

An output device 4290 in accordance with the present technology may take the form of one or more of a visual, audio and haptic unit. A visual display may be a Liquid Crystal Display (LCD) or Light Emitting Diode (LED) display.

5.5.2.9.1 Display Driver 4292

A display driver 4292 receives as an input the characters, symbols, or images intended for display on the display 4294, and converts them to commands that cause the display 4294 to display those characters, symbols, or images.

5.5.2.9.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5.3 PAP Device Algorithms 4300

5.5.3.1 Pre-Processing Module 4310

A pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: PI pressure estimation 4412, vent flow 4414, leak flow 4316, respiratory flow 4318, and jamming detection.

5.5.3.1.1 Respiratory Flow 4318

As shown in a model typical breath waveform in FIG. 6A, the magnitude of expiratory flow may not be constant within a breath, but may vary over time. As the magnitude of expiratory flow may not be constant within a breath, determination of the expiratory flow rate as it varies may be desirable. In one form of the present technology, a respiratory flow estimation algorithm 4318 receives as an input a flow generator flow rate, $Q_{FG}$, a vent flow rate, Qv, and a leak flow rate, Ql, and estimates a respiratory flow rate of air, Qr, of the patient, by subtracting the vent flow rate Qv and the leak flow rate Ql from the flow generator flow rate. $Q_{FG}$.

In some cases, such as when a vent valve 4450 blocks fluid communication between the patient interface 3000 and the blower 4142, some or all of the above inputs such as the vent flow rate, Qv, leak flow rate. Ql, or the flow generator flow rate, $Q_{FG}$, may not be available or do not correlate adequately to the respiratory flow rate, Qr. In one form of the present technology, the respiratory flow estimation algorithm 4318 may comprise an expiratory flow model. $EXP_{model}$, to determine an expiratory characteristic such as the respiratory flow rate, without direct measurement. The expiratory flow model, $EXP_{model}$, and/or the expiratory characteristics determined using the expiratory flow model may also be used to determine the pressure in the patient interface 3000 as will be described in further detail below.

FIG. 9 shows one form of a typical breath flow waveform profile, wherein a measure of the respiratory flow is not available during the expiratory portion of the breath cycle. In such a case the expiratory flow rate may vary over the time of expiration but may not be directly measured. In one form of the present technology, an expiratory flow model, $EXP_{model}$, as shown in FIG. 10 may be used to estimate the expiratory flow rate and its variation across the time of expiration.

Using this form of the expiratory flow model, $EXP_{model}$, an expiratory flow rate, Qexp, at a time $T_1$ may be determined without a direct measurement. For example, the expiratory flow rate, Qexp, at the time $T_1$ may be determined based on its relationship to a reference time, such as a time of start of expiration $T_0$, using the elapsed time $\Delta T$. Another suitable reference time may be a time of end of inspiration, for example detected by falling of a respiratory flow rate to below a threshold level. Alternatively, where the treatment system comprises a flow sensor 4274 and the variable vent 4400 comprises a flexible divider vent valve 4460, detection of a decrease in the measured flow generator flow rate $Q_{FG}$ to below a threshold level for longer than a threshold period of time may determine a suitable reference time. Levels of suitable threshold levels and/or the threshold period of time may vary according to each arrangement of the technology. In another arrangement wherein the treatment system comprises a flow sensor 4274 and the variable vent 4400 comprises a servo-controlled vent valve, receipt of a vent valve configuration signal indicating a configuration of the servo-controlled vent valve, may determine a suitable reference time. For example, the vent valve configuration signal may indicate that the servo-controlled vent valve is configured to block flow between the blower 4142 and the variable vent 4000. As a further alternative, inspiratory effort and/or expiratory effort may be detected, and the reference time may be determined based on the detection of an end of inspiratory effort and/or commencement of expiratory effort. Methods of detecting inspiratory effort and/or expiratory effort, as well as characteristics of inspiration and/or expiration described in PCT application publications number WO 2006/079152, WO 2010/121313 and/or WO 2012/024733, all of which are incorporated herewithin by reference, may also be used to determine a suitable reference time.

In one form of the expiratory flow model, $EXP_{model}$ as shown in FIG. 1, the expiratory flow rate, $Q_{E1}$, at a time, $T_{E1}$, may be estimated based on how much time has passed since the start of expiration of the current breath, $T_{Estart}$. The time between $T_{E1}$ and $T_{Estart}$ may be referred to as the change in time, $\Delta T_1$. The corresponding change in flow rate, $\Delta Q_1$, at time $\Delta T_1$ may be obtained from the expiratory flow model, $EXP_{model}$, and used to estimate $Q_{E1}$. Similarly, the corresponding flow rate $Q_{E2}$ at a time $T_{E2}$ may be estimated by the change in flow rate $\Delta Q_2$, at a change in time $\Delta T_2$ from the expiratory flow model $EXP_{model}$.

The expiratory flow model, $EXP_{model}$, may comprise effects of or be derived with some or all of the following parameters of the respiratory system and/or the pneumatic path of the treatment system: parts of the patient's respiratory system, leak flow, the patient interface 3000, the air circuit 4170, the vent 4400 and/or the vent valve 4450. For example, the resistance, inertance and/or compliance of the patient's respiratory system, as well as a ventilation volume, a tidal volume (e.g., the measured inspired volume from the immediately preceding inspiratory portion of the particular respiratory cycle for which the expiratory model will be applied), a peak inspiratory flow, an average length of time in inspiration, a length of previous inspiration, a lung compliance and/or a lung resistance may be included in the expiratory model, as may be flow impedance of the air circuit 4170, the flow impedance of the variable vent 4400 and/or the flow impedance of the vent valve 4450. The expiratory flow model. $EXP_{model}$, may comprise a sub-model such as a model of the respiratory system of the patient 1000, which may comprise one or more of the parameters of the respiratory system. Another form of a suitable sub-model may be a model of the pneumatic path of the treatment system including such components as the patient interface 3000, the air circuit 4170, the variable vent 4400 and/or the vent valve 4450. Any single or combination of the preceding parameters may be included to modify the expiratory flow model. $EXP_{md}$. It would be understood by those skilled in the art that the expiratory flow model may also be built or calculated based on other parameters and/or characteristics.

It should be noted that the term impedance in the context of this specification in relation to the treatment system, and in particular in relation to the variable vent 4400, is used to primarily refer to resistance unless stated otherwise. In the art, the term impedance may be used as a combination of resistance, compliance and inertance. However, in the context of this specification, impedance is primarily used to refer to resistance. Furthermore, as will be described below, the term impedance is primarily used in connection with the treatment system, where the effect of system compliance and inertance may be neglected in some modelling methods.

Accordingly, the expiratory flow model. $EXP_{model}$, may be used to determine other expiratory characteristics than the expiratory flow rate. For example, the expiratory flow model, $EXP_{model}$, may be used to determine the pressure in the patient interface 3000, such as for controlling expiratory pressure based on the determined pressure or determining a target setting for expiratory pressure based on the determined pressure, or the phase of expiration. In some cases, one or more aspects of the expiratory flow model may be determined based on a measure of the patient's respiration, such as a measure of inspiration. For example, a measure of ventilation volume, tidal volume, peak inspiratory flow and/or a length of time in inspiration. Also measures of lung compliance and/or lung resistance may be used in the model.

FIGS. 11A and 11B illustrate additional models that may be determined/calculated and/or applied in some versions of the present technology. In this regard, the previously discussed model of FIG. 11 is calculated to more closely model a flow verse time curve of typical patient expiration. In FIGS. 11A and 11B a sloped and/or stepped model is applied such as in a linear fashion. In some cases, the model may be formed based on values sensed during the inspiratory portion of the breath (e.g., inspiratory volume and time) when the distally located sensor (e.g., at or near the blower) represents conditions of the patient interface. For example, the slope and amplitude of the model of FIG. 11A may be determined such that the expiratory volume of the inverted sawtooth equals the measured inspiratory volume and the expiratory time of the inverted sawtooth is a proportion of the measured inspiratory time. Similarly, the inverted step function of the model of FIG. 11B may be determined such that the expiratory volume of the step equals the measured inspiratory volume and the expiratory time for the step is a proportion of the measured inspiratory time.

Accordingly, in the example of FIG. 11A, the expiratory flow rate, $Q_{A1}$, at a time, $T_{E1}$, may be estimated based on how much time $T_{A1}$ has passed since the start of expiration of the current breath, $T_{Estart}$, according to a desired slope such as determined from a maximum expiratory flow rate A occurring at $T_{Estart}$ and a desired expiratory flow rate decrease angle Φ (e.g., slope). Similarly, the corresponding flow rate $Q_{A2}$ at a time $T_{E2}$ may be estimated from the maximum expiratory flow rate A by the flow rate decrease angle and a time change such as a change in time $\Delta T_2$ according to the expiratory flow model $EXP_{model}$.

By way of further example in FIG. 11B, the expiratory flow rate at a time, $T_{E1}$, may be estimated based on a square wave given how much time $T_{A1}$ has passed since the start of expiration of the current breath, $T_{Estart}$, according to a desired time and amplitude characteristic of the square wave such as determined from a maximum expiratory flow rate A occurring at $T_{Estart}$. Similarly, the corresponding flow rate at a time $T_{E2}$ before inspiration may be estimated from the square wave expiratory flow model $EXP_{model}$ so as to have for example, a nominal or zero flow rate.

5.5.3.1.2 Respiratory Circuit Model

The prior art literature describes numerous methods of varying complexity to model the respiratory system. The choice of one particular model over another may depend on each model's properties such as its perceived strengths and weaknesses. In one form. Lorino et al. discuss three commonly used visco-elastic models: the Mead. Otis and Mount models. Rodarte and Rehder suggest that a lung model based on the Mead model may be suitable for use in a control algorithm. As discussed by Lorino et al., visco-elastic models are commonly used to model systems involving mechanical ventilation. Common models, such as the Mead, Otis and Mount models involve the combination of Maxwell and Kelvin bodies in different arrangements. One advantage of visco-elastic models, from a control systems perspective, is said to be that it may be readily characterized by a linear differential equation. A visco-elastic model may be used in one form of the respiratory circuit model; however a person skilled in the art would understand that other forms of the respiratory circuit models would be suitable for use with the present technology.

In one form, Rodarte and Rehder model the properties of a lung as an electrical circuit. FIG. 12a shows a simplified representation of a lung where the lung is represented as a single compartment mechanical model. Using this model, airway resistance ($R_{AIRWAY}$) is analogous to an electrical resistor, lung compliance ($C_{LUNG}$) is analogous to capacitance and airway inertance ($L_{AIRWAY}$) is analogous to inductance. Patient effort, that is, the action of the muscles to change lung volume can be modelled as a pressure source acting on the passive elements in the system. The model can then be represented as an electrical circuit as shown in FIG. 12b.

The contribution of airway inertia is related to the density of air and so this value may be assumed to be a constant. Under this assumption, the remaining variable parameters for each patient 1000 under steady state conditions are lung compliance ($C_{LUNG}$) and airway resistance ($R_{AIRWAY}$). In one form, values of lung compliance ($C_{LUNG}$) and airway resistance ($R_{AIRWAY}$) determined for the specific patient 1000 may be used, for example based on measures of respiration, or by providing input values unique to each patient 1000, such as their height, weight and/or medical conditions. In another form, lung compliance ($C_{LUNG}$) and airway resistance ($R_{AIRWAY}$) may be modelled as generic values, for example based on median values across a population of interest. One exemplary set of suitable values of above parameters may be lung compliance ($C_{LUNG}$) of 30 ml/cmH$_2$O, airway resistance ($R_{AIRWAY}$) of 2.5 cmH$_2$O/l/s, and airway inertance ($L_{AIRWAY}$) of 0.014 cmH$_2$O/l/s/s.

According to one aspect, the respiratory circuit model may comprise effects of the inspiratory muscle activation, preferably only during a part of expiration such as the first third of expiration where its effect is not negligible. Muscle activation may act as a braking force on the development of the peak expiratory flow by slowing the initial expiratory flow from the lungs. This muscular contribution may be included in the respiratory circuit model as a time-variant non-linearity in one form. In some forms, effects of the inspiratory muscle activation may be omitted from the respiratory circuit model.

In one form, the following model may be formulated to determine the pressure at the entrance of the respiratory circuit (P) based on the lung compliance ($C_{LUNG}$), airway resistance ($R_{AIRWAY}$) airway inertia ($L_{AIRWAY}$), volume of the respiratory circuit ($V_{RESP}$), rate of change (first derivative) of the respiratory circuit volume ($\dot{V}_{RESP}$) and the rate of change of the rate of change (second derivative) of the respiratory circuit volume ($\ddot{V}_{RESP}$).

$$P = \frac{1}{C_{LUNG}} V_{RESP} + R_{AIRWAY} \dot{V}_{RESP} + L_{AIRWAY} \ddot{V}_{RESP} \quad \text{(Eq. 1)}$$

The above differential equation may be then solved to control the pressure in respiratory circuit, and in turn control the pressure in the patient interface, as they are in fluid communication with each other. The above formulation neglects the effect of muscle activity such as inspiratory muscle activation, and it may be modified to incorporate the effect of muscle activity in some cases. For example, pressure due to muscle activity $P_{Mus}$ may be included by modifying the above formulation as follows.

$$P = \frac{1}{C_{LUNG}} V_{RESP} + R_{AIRWAY} \dot{V}_{RESP} + L_{AIRWAY} \ddot{V}_{RESP} + P_{Mus} \quad \text{(Eq. 2)}$$

The rate of change of the respiratory circuit volume ($\dot{V}_{RESP}$) may be the same as the respiratory flow rate Qr in some cases.

In the above model the terms airway resistance and lung compliance may be taken to mean the total equivalent values of resistance and compliance for the entire respiratory system. However, in some cases the values may be derived from a more complex model in which the impedance is broken up into a finer resolution. The upper respiratory tract, including the mouth, nose and larynx may also contribute to the resistance and compliance affecting the air path and may change depending on the breathing route utilized by the person. In some cases it may be desirable to separately model the upper and lower airway resistances, and/or to model them differently according to the direction of the respiratory flow. Accordingly, their effects may be further included in the respiratory circuit model in some cases.

In some cases, the expiratory portion of a breath may not follow a predictable pattern. Airway obstructions such as those caused by asthma, COPD or anxiety may result in a breathing pattern that may not be passive and so follow a different expiratory pattern. The prior art literature indicates that there may be a number of measures such as inspiration time and peak inspiratory flow which can be indicative of different breathing patterns. The expiratory flow model may include the above measures for improved performance where such irregular expiratory patterns occur. *The Physiology Handbook—The Respiratory System* is an example of prior art that details how breath patterns change in different clinical conditions and exemplary indicators of these conditions.

5.5.3.1.3 Vent Flow Algorithm 4414

In one form of the present technology, a vent flow estimation algorithm 4414 receives as an input an estimated pressure, Pm, in the patient interface 3000 and estimates a vent flow of air, Qv, from a continuous vent 3400, such as a fixed continuous vent.

In another form of the present technology, the vent flow estimation algorithm 4414 receives as an input an estimated patient respiratory flow rate, and estimates a vent flow of air, Qv. The vent flow estimation algorithm 4414 may also receive further inputs in estimating the vent flow of air, such as a flow impedance of the variable vent 4400, the vent valve 4450, and/or an estimate pressure in the patient interface 3000. The flow impedance of the vent valve 4450 may have a significant effect on the total impedance to the flow of exhaust gas. In some forms of the present technology as described above, the flow impedance of the vent valve 4450 may be variable, in arrangements that use a servo-controlled vent valve as the vent valve 4450 or a flexible divider vent valve 4460. In such cases, the effects of vent valve flow impedance may also be included in the vent flow estimation algorithm 4414.

The vent flow may be also determined in some cases using the expiratory flow model, $\text{EXP}_{model}$, such as when the vent valve 4450 blocks fluid communication between the blower 4142 and the variable vent 4400, while allowing fluid communication between the variable vent 4400 and the patient interface 3000. In this case, as shown in FIG. 15, the vent flow, Qv, may be determined by subtracting the leak flow, Ql, from the expiratory flow rate, $Q_{exp}$, which may be determined from the expiratory flow estimation algorithm 4318.

5.5.3.1.4 Patient Interface (PI) Pressure Estimation 4412

A PI pressure estimation algorithm 4412 estimates the pressure in the patient interface 3000, and provides as an output an estimated pressure, Pm, in the patient interface 3000.

In one form of the present technology, the PI pressure estimation algorithm 4412 receives as an input a signal indicative of the pressure in the pneumatic path proximal to an outlet of the pneumatic block 4020. The PI pressure estimation algorithm 4412 may determine the pressure in the patient interface 3000 based on a correlation between the pressure in the pneumatic path proximal to an outlet of the pneumatic block 4020 and the pressure in the patient interface 3000. In one arrangement of the present technology, the correlation between the pressure in the pneumatic path proximal to an outlet of the pneumatic block 4020 and the pressure in the patient interface 3000 may be estimated in the form of a pressure drop in the air circuit 4170. In some cases the combination of the flow through the variable vent 4400 and the leak flow may account for all of the impedance from the patient interface 3000 to atmosphere, and in such cases the pressure in the patient interface may be represented as a function of the respiratory flow, the leak flow, and the variable vent 4400 impedance. In this situation knowledge of the variable vent 4400 impedance along with a good estimate of the respiratory flow and the leak flow may be adequately used to determine the pressure in the patient interface 3000.

In another arrangement according to the present technology, a vent valve 4450 may selectively block fluid communication between the pneumatic block 4020 and the patient interface 3000. In such an arrangement, the pressure in the pneumatic path proximal to an outlet of the pneumatic block 4020 may not have a correlation to the pressure in the patient interface 3000. The PI pressure estimation algorithm 4412 may use correlations to other parameters to determine the pressure in the patient interface 3000. In some forms, the PI pressure estimation algorithm 4412 may receive as inputs outputs produced by the expiratory flow model and/or the respiratory circuit model. In other forms, the PI pressure estimation algorithm 4412 may comprise parts or the entirety of the expiratory flow model and/or the respiratory circuit model.

Examples of parameters or characteristics that may affect the pressure in the patient interface 3000 include total impedance to the flow of exhaust gas and the magnitude of expiratory flow. There may also be any number of other parameters and/or characteristics which may be used to determine the pressure in the patient interface 3000, such as, but not limited to, those used above in the expiratory flow model and/or the respiratory circuit model. Namely, lung compliance ($C_{LUNG}$), airway resistance ($R_{AIRWAY}$), airway inertia ($L_{AIRWAY}$), volume of the respiratory circuit ($V_{RESP}$), rate of change of the respiratory circuit volume ($\dot{V}_{RESP}$), the rate of change of rate of change of the respiratory circuit volume ($\ddot{V}_{RESP}$) and effect of muscle activity. Resistance and compliance of other parts of the respiratory circuit such as the upper respiratory tract, including the mouth, nose and larynx may also be included. Any other components of the treatment system such as the air circuit 4170, patient interface 3000 and/or the variable vent 4400 may also be characterised based on its own resistance, compliance and inertia, and added to the model as required.

One form of the PI pressure estimation algorithm 4412 may be as follows:

$$P_m = \frac{1}{C_{TOT}} V_{TOT} + R_{TOT} \dot{V}_{TOT} + L_{TOT} \ddot{V}_{TOT} \quad \text{(Eq. 3)}$$

In the above equation, $R_{TOT}$ represents the combined resistance of the following components: the respiratory system, the patient interface 3000, the air circuit 4170 and the variable vent 4400. $C_{TOT}$ represents the combined resistance of the following components: the respiratory system, the patient interface 3000, the air circuit 4170 and the variable vent 4400. $L_{TOT}$ represents the combined inertance of air in the following components: the respiratory system, the patient interface 3000, the air circuit 4170 and the variable vent 4400. $V_{TOT}$ represents the combined volume of the following components: the respiratory system, the patient interface 3000, the air circuit 4170 and the variable vent 4400. $\dot{V}_{TOT}$ and $\ddot{V}_{TOT}$ represent first and second derivatives of $V_{TOT}$. The terms $R_{TOT}$, $C_{TOT}$ and/or $L_{TOT}$ may be constants in some forms of the present technology; however they may be variable in other forms. For instance, the term $R_{TOT}$ may vary to indicate the varying impedance of the variable vent as will be described in further detail below. In some forms of the present technology, the terms $R_{TOT}$, $C_{TOT}$ and/or $L_{TOT}$ may be predetermined, however they may also be determined for each patient, for example using a measure of respiration of the patient, or during a calibration phase. In some arrangements of the present technology, the compliance and/or inertance of components of the treatment system such as the patient interface 3000, the air circuit 4170 and the variable vent 4400 may be relatively small in relation to the compliance and/or inertance of the respiratory circuit. Accordingly, the values of compliance and/or inertance of the respiratory circuit may be suitable representative values for combined compliance and/or inertance. One example set of suitable values of above parameters may be combined compliance ($C_{TOT}$) of 30 ml/cmH$_2$O, combined resistance ($R_{TOT}$) of 5 cmH$_2$O/l/s, and combined inertance ($L_{TOT}$) of 0.014 cmH$_2$O/l/s/s.

In one form, the PI pressure estimation algorithm 4412 may operate based on the above equation (Eq. 3) by implementing an iterative solution with constant values of $C_{TOT}$, $R_{TOT}$, $L_{TOT}$, $V_{TOT}$, providing an initial estimate of $\ddot{V}_{TOT}$ and solving for $\ddot{V}_{TOT}$ to determine an updated value of $\ddot{V}_{TOT}$. One suitable initial estimate of $\ddot{V}_{TOT}$ may be a product of the pressure of the flow of breathable gas and the combined compliance. The updated value of $\ddot{V}_{TOT}$ may be fed back into the control system to update the value of $\dot{V}_{TOT}$ by the integral of $\ddot{V}_{TOT}$, such as the product of frequency of the iterative solution and the $\ddot{V}_{TOT}$. Similarly, $V_{TOT}$ may be updated by the integral of $\dot{V}_{TOT}$, such as the product of frequency of the iterative solution and the $\dot{V}_{TOT}$.

According to one arrangement of the present technology, the majority of the expiratory flow may be exhausted as a flow of exhaust gas through the variable vent 4400. Also, the total impedance to the flow of exhaust gas may correlate strongly to the flow impedance of the variable vent 4400. In such an arrangement, a suitable PI pressure estimation algorithm 4412 may comprise the effects of the flow impedance of the variable vent 4400 and/or the effects of the magnitude of exhaust flow through the variable vent 4400 to determine the pressure in the patient interface 3000, for example by knowing (e.g., by determining the patient interface pressure (PI)) the value of $R_{TOT}$. In this arrangement it follows that the pressure in the patient interface 3000 may be controlled by varying $R_{TOT}$.

In arrangements where a servo-controlled vent valve is used as the vent valve 4450, the PI pressure estimation algorithm 4412 may comprise an indicator of the impedance of the servo-controlled vent valve. Some of the suitable indicators of the impedance of the servo-controlled vent valve may comprise a position of a movable component of the servo-controlled vent valve or a position of an actuator configured to drive the servo-controlled vent valve.

In one form, the flexible divider vent valve 4460 may comprise a membrane 4462 as shown in FIG. 8A and FIG. 8B, whose deflection may affect the flow impedance. In some arrangements, the blower 4142 may be used to change a pressure on a first side of the membrane 4462 thereby changing the pressure differential and thus deflection of the membrane as described in further detail above. According to this form, it may be appropriate for the PI pressure estimation algorithm 4412 to comprise the effects of pressure on the blower side of the membrane. One suitable signal that is indicative of pressure on the blower side of the membrane may be a signal of a rotational speed of the blower. Others may include a signal of pressure measured between the blower and the membrane 4462, a signal of deflection of the membrane 4462, or a signal indicating the electrical current that is drawn by the blower, although any number of other signals may be possible. The PI pressure estimation algorithm 4412 may also comprise a signal that is indicative of the differential pressure between the first side and the second side of the membrane 4462, such as a strain on the membrane 4462, or an optical measurement of the deflection of the membrane 4462.

It should be understood that a 'model', in the present context, as in 'expiratory model' or 'expiratory flow model', may be implemented in one or more of a variety of forms known to those skilled in the art. For example, a model may be based on a single or multi-dimensional look-up table, such as one with pre-calculated or pre-determined values of the above relationships or equations, wherein one or more input parameters are used to find, or 'look-up' an output value. Alternatively, a model may be based on a mathematical relationship such as, but not limited to, a single or multi-variable equation, which may include linear, polynomial, exponential, logarithmic, or any number of other forms.

5.5.3.1.4.1 Variable Flow Impedance Vent

According to some arrangements of the present technology, the flow impedance of the variable vent 4400 and/or the vent valve 4450 may be variable as described in greater detail previously. In such arrangements, the effects of variable flow impedance may be incorporated into the expiratory flow model and/or the PI pressure estimation algorithm 4412.

5.5.3.1.5 Leak Flow Algorithm 4316

In one form of the present technology, a leak flow algorithm 4316 receives as an input a total flow, Qt, and a vent flow Qv, and provides as an output a leak flow Ql by calculating an average of Qt-Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt-Qv, and low pass filtered square root of pressure Pm, where the low pass filter time constant has a value sufficiently long to include several breathing cycles. e.g. about 10 seconds.

In another form, the leak flow algorithm 4416 receives as an input a respiratory flow Qr during expiration (also referred herein as patient expiratory flow Qexp), and an estimated pressure, Pm, in the patient interface 3000, and provides as an output a leak flow Ql. The leak flow algorithm 4416 may determine the leak flow Ql by calculating a leak conductance, and determining a leak flow Ql to be a function of leak conductance and pressure. Pm as shown in FIG. 15. According to some arrangements of the present technology, the leak flow algorithm 4416 may calculate leak conductance during an inspiratory portion of the breath cycle.

A basis of another form of a leak flow algorithm 4316 is shown in FIG. 14A-FIG. 14B. FIG. 14A shows a longer form of a model typical breath waveform as shown in FIG. 6A, showing two breath cycles. The breath waveform shown in FIG. 14A includes a constant leak flow with magnitude $Q_{leak1}$ to indicate a total flow rate $Q_{tot}$. One outcome of such a constant leak is that the breath waveform is shifted upwards by an offset with magnitude $Q_{leak1}$. As described above, the variable vent valve 4450 may be configured to block fluid communication between the variable vent 4400 and the patient interface 3000 during inspiration. In the absence of intrinsic PEEP (Positive End Expiratory Pressure), which is a particular patient condition where the expiratory flow doesn't approach zero at the end of expiration, at time $T_{inflection}$, the patient respiratory flow $Q_r$ would be zero, and thus the total flow would be equal to the constant leak flow $Q_{leak1}$. Thus the sensed flow at time $T_{inflection}$ would equal the leak flow $Q_{leak1}$. In one form, the total flow rate at time $T_{inflection}$ may be sensed by the flow transducer as total flow is positive and thus the blower 4142 would be in fluid communication with the patient interface 3000. The measured flow rate $Q_{meas}$ may appear as shown in FIG. 14B. In this example, the time $T_{inflection}$ may be determined by monitoring the rate of change of the total flow $Q_{tot}$, and finding the point of inflection (such as based on calculation of a second derivative and determining if it is zero, etc.) where the behaviour of the respiratory system switches from expiration to inspiration and creates an inflection point. In the presence of intrinsic PEEP, an estimate of the unintentional leak, $Q_{leak1}$, may be determined by subtracting an estimate of the magnitude of patient flow at the point of inflection $T_{inflection}$ from the total flow.

5.5.3.2 Therapy Engine Module 4320

In one form of the present technology, a therapy engine module 4320 receives as inputs one or more of a pressure, Pm, in a patient interface 3000, and a respiratory flow rate of a patient, Qr, and provides as an output, one or more therapy parameters.

In one form of the present technology, a therapy parameter is a CPAP treatment pressure Pt.

In one form of the present technology, a therapy parameter is one or more of a level of pressure support, and a target ventilation.

5.5.3.2.1 Phase Determination 4321

In one form of the present technology, the PAP device 4000 does not determine phase.

In one form of the present technology, a phase determination algorithm 4321 receives as an input a signal indicative of respiratory flow rate, $Q_r$, and provides as an output a phase of a breathing cycle of a patient 1000.

In one form, the phase output is a discrete variable with values of either inhalation or exhalation.

In one form, the phase output is a discrete variable with values of one of inhalation, mid-inspiratory pause, and exhalation.

In one form, the phase output is a continuous variable, for example varying from 0 to 1, or 0 to 2Pi.

In one form, the phase output is determined to have a discrete value of inhalation when a respiratory flow rate Qr has a positive value that exceeds a positive threshold. In one form, a phase is determined to have a discrete value of exhalation when a respiratory flow rate Qr has a negative value that is more negative than a negative threshold.

In some forms, such a process may be implemented for determining whether or not a sensor for sensing a gas characteristic of the patient interface is blocked such that the sensor may not get a measure indicative of the gas characteristic. This may occur when the blocking is cyclical or has phases, such as when the conduit to the sensor is subject to expiratory blocking with example venting apparatus described herein (e.g., any of the valves of FIGS. 7A-7B and 8A-8C). Such a process may then serve as logic for choosing different processes for system control given the cyclical nature of the incapacitation of the sensor with respect to its ability to sense the patient interface gas characteristic. Detection of such presence or absence of blocking or expiratory blocking may be implemented with detection of, for example, end of inspiration or beginning of inspiration, such as by evaluation of a measure of flow or pressure from a signal from a sensor and a threshold. Other similar detection processes may also be implemented.

5.5.3.3 Pressure Control Module 4330

A pressure control module 4330 in accordance with one aspect of the present technology receives as an input a target patient interface (PI) pressure Pt, and controls a pressure device 4140 to deliver that pressure to the patient 1000.

A pressure control module 4330 in accordance with one aspect of the present technology receives as an input a target EPAP pressure and a target IPAP pressure, and controls a pressure device 4140 to deliver those respective pressures.

A flow chart with processes according to one form of the present technology is shown in FIG. 13. In this example, a processor may be implemented with programming logic to select between different pressure detection and/or control processes (e.g., second process 4412-A of FIG. 13 and first process 4412-B of FIG. 13) depending on blocking and unblocking of a sensor's ability to detect a gas characteristic of the patient interface. That is, when the sensor is blocked, the system is in a state where the sensor (e.g. blower-proximate sensor) is able to measure pressure but the measured pressure no longer indicates conditions at the patient end of the therapy system. These processes may be cyclically selected such as in the case of cyclical blocking and unblocking (e.g., inspiratory un-blocking and expiratory blocking.) Thus, a pressure control of a controller, such as closed loop pressure control, may operate with different or alternating functions in conjunction with the selection of the multiple (e.g., first and second) processes when the current measure of pressure, due to blocking, does not accurately reflect the system being controlled at all times. Such a system may control pressure in the patient interface without a pressure sensor at or in the patient interface, such as where the pressure sensor is located at or near the blower or flow generator, across a delivery conduit and away from the patient interface when some system component or variable condition may interfere (e.g. block) the detection of the patient interface condition (e.g., pressure) with the sensor.

For example, interface gas pressure in the patient interface proximate a patient airway may be determined in the first process 4412-B from a current measure of pressure from the sensor if the conduit to the sensor is unblocked (e.g., at or during inspiration). Such a determination of interface gas pressure may be made from a pressure drop associated with a delivery conduit characteristic and the current measure of pressure. The first process may optionally determine a pressure adjustment for pressure in the patient interface from a difference between the interface gas pressure and a target pressure.

Similarly, interface gas pressure in the patient interface proximate a patient airway may be determined in the second process 4412-A, such as without a current measure of pressure from the sensor or a sensor near the patient interface, if the conduit to the sensor is blocked (e.g., at or during expiration). In such a process, interface gas pressure in the patient interface proximate a patient airway may be determined from a modelled flow estimate in presence of blocking of the conduit to the sensor (e.g., from a respiratory flow estimation 4318 process). The modelled flow estimate may be an estimate of expiratory flow as discussed in more detail herein. The determined interface gas pressure may be calculated from an elapsed time, such as by detecting an end of inspiration, and from the expiratory flow estimate. The second process may determine a pressure adjustment for pressure in the patient interface from a difference between the determined interface gas pressure and a target pressure.

Optionally, a common pressure control module 4330 may receive as an input a value of PI pressure from the PI pressure estimation module 4412 (e.g., 4412-A and/or 4412-B). The pressure control module 4330 may then compare the value of PI pressure to the target PI pressure to determine a pressure error value and accordingly adjust the PI pressure based on the pressure error value.

In one arrangement of the present technology, the pressure control module 4330 may change the impedance of the vent valve 4450 to control the pressure in the patient interface 3000 as described in further detail above.

According to one form, the pressure control module 4330 may receive as inputs signals indicating one or all of the following: flow impedance of the vent valve 4450, flow impedance of the variable vent 4400 and/or pressure in the patient interface 3000.

5.5.3.4 Detection of Fault Conditions 4340

In one form of the present technology, a processor executes one or more methods for the detection of fault conditions. Preferably the fault conditions detected by the one or more methods includes at least one of the following:
Power failure (no power, or insufficient power)
Transducer fault detection
Failure to detect the presence of a component
Operating parameters outside recommended ranges (e.g. pressure, flow, temperature. $PaO_2$)
Failure of a test alarm to generate a detectable alarm signal.

Upon detection of the fault condition, the corresponding algorithm signals the presence of the fault by one or more of the following:
Initiation of an audible, visual &/or kinetic (e.g. vibrating) alarm
Sending a message to an external device
Logging of the incident

5.6 Humidifier 5000

5.6.1 Humidifier Overview

In one form of the present technology there is provided a humidifier 5000 comprising a water reservoir 5110 and a heating plate 5120. The humidifier 5000 may be a separable component to the PAP device 4000, or alternatively may be integrally constructed with the PAP device 4000.

5.6.2 Humidifier Mechanical Components 5100

5.6.2.1 Water Reservoir 5110

According to one aspect of the present technology the humidifier 5000 comprises a water reservoir 5110 as shown in FIG. 5b. The water reservoir 5110 may be configured so that the flow of breathable gas would be further humidified as it passes through the interior of the water reservoir 5110.

The reservoir 5110 may be configured to hold, or retain, a body of liquid, such as water. The body of liquid is evaporated to add humidity to the flow of breathable gas, typically in the reservoir 5110. In some cases, the humidifier 5000 may be in continuous use for a period of up to several hours, such as between four to ten hours. The reservoir may be configured to hold a predetermined maximum volume of liquid of several hundred milliliters to provide humidification for the duration of this period.

According to one aspect, the water reservoir 5110 may provide an internal path for the flow of breathable gas to travel between a reservoir inlet and a reservoir outlet. In some instances, the internal path for the flow of breathable gas may be arranged tortuously to increase the time that the flow of breathable gas spends within the reservoir 5110 to increase humidity added to the flow of breathable gas.

The internal volume of the water reservoir 5110 may be arranged to reduce likelihood of any water being spilled in the reverse direction, upstream of the humidifier 5000. This may be done in one of a number of ways, such as providing additional internal volume, an elongated inlet tube, a valve or a divider, so that any water contained within the humidifier 5000 would not reach the reservoir inlet at any orientation.

In some arrangements, the water reservoir 5110 may comprise a conductive portion configured to introduce heat to the reservoir 5110. The conductive portion may be coupled with a heating element 5240 to introduce heat to the interior of the water reservoir 5110. Suitable materials for construction of the conductive portion may include aluminium or another heat conducting material. In some forms, the water reservoir 5110 may comprise a heating element 5240. According to one arrangement, the heating element 5240 may be moulded into a resin forming a tub, as disclosed in the PCT patent application WO 2008/148154, the contents of which is incorporated herein by reference.

5.6.2.2 Heating Plate 5120

According to another aspect of the present technology, the humidifier 5000 may comprise a heating plate 5120 which is used to transfer heat to the water reservoir 5110 as shown in FIG. 5*b*. The heating plate 5120 may comprise a heating element 5240 located on or near the base of the humidifier 5000. The heating plate 5120 may be formed, for example, of a nickel chrome alloy, stainless steel or anodised aluminium.

5.6.3 Humidifier Electrical & Thermal Components 5200

A humidifier 5000 may comprise a number of electrical and/or thermal components such as those listed below.

5.6.3.1 Sensors

A humidifier 5000 may comprise one or more sensors, such as an air pressure sensor(s) 5210, an air flow sensor(s), a temperature sensor(s) 5220 and/or a relative humidity sensor(s).

5.6.3.2 Heating Element(s) 5240

The heating element 5240 may be a heat generating component such as an electrically resistive heating track. One suitable example of a heating element 5240 is a layered heating element such as one described in the PCT Patent Application Publication Number WO 2012/171072, the entire document of which is incorporated herewithin by reference.

5.633 Humidifier Controller 5250

According to one arrangement of the present technology, a humidifier 5000 may comprise a humidifier controller as shown in FIG. 5*c*. The humidifier controller may be a part of the central controller, or may be a separate controller, which may be in communication with the central controller. The humidifier controller may be configured to receive input signals from one or more sensors such as measures of characteristics of the flow of breathable gas, measures of characteristic of the water in the reservoir 5110, measures of characteristics of the reservoir 5110 or measures of characteristics of the humidifier 5000. The humidifier controller may also be configured to execute or implement humidifier algorithms and/or deliver one or more output signals. The humidifier controller may comprise a heated tube controller configured to control the temperature of a heated tube and/or a hot plate controller configured to control the temperature of a hot plate.

5.7 Humidity Exchanger

In one form of the present technology there a humidity exchanger may be implemented such as described in Patent Cooperation Treaty Patent Application Publication Number WO 2013/067592, which may be located between a variable vent 4400 and the patient interface 3000. The humidity exchanger may serve to extract moisture from the expiratory flow and return some of that moisture to the inspiratory flow. In one form the humidity exchanger may present significant impedance that may be included in the above model for the purpose of estimating the respiratory flow and/or controlling the patient interface 3000 pressure. In one form the humidity exchanger impedance may be considered to be negligible and not included in the model.

5.8 Breathing Waveforms 6000

A model typical breath waveform of a person while sleeping is shown in FIG. 6A. While the parameter values may vary, a typical breath may have the following approximate values: tidal volume, Vt, 0.5 L, inhalation time, Ti, 1.6 s, peak inspiratory flow rate, Qpeak, 0.4 Us, exhalation time. Te, 2.4 s, peak expiratory flow rate, Qpeak, −0.5 Us. The total duration of the breath, Ttot, is about 4 s. The person typically breathes at a rate of about 15 breaths per minute (BPM), with minute ventilation, or ventilation, Vent, about 7.5 L/minute. A typical duty cycle, the ratio of Ti to Ttot is about 40%.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, the term 'air' may be used interchangeably with 'breathable gas'. Typically, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to a reference pressure, typically atmospheric pressure

5.9.2 Aspects of PAP Devices

APAP: Automatic Positive Airway Pressure. Positive airway pressure that is continually adjustable between minimum and maximum limits, depending on the presence or absence of indications of SDB events.

Therapy: Therapy in the present context may be one or more of positive pressure therapy, oxygen therapy, carbon dioxide therapy, control of dead space, and the administration of a drug.

5.9.3 Aspects of the Respiratory Cycle

Breathing rate: The rate of spontaneous respiration of a patient, usually measured in breaths per minute.

Expiratory portion of a breathing cycle: The period from the start of expiratory flow to the start of inspiratory flow.

Inspiratory portion of a breathing cycle: Preferably the period from the start of inspiratory flow to the start of expiratory flow will be taken to be the inspiratory portion of a breathing cycle.

Tidal volume (Vt): The volume of air inhaled or exhaled during normal breathing, when extra effort is not applied.

Inhalation time (Ti): The duration of the inspiratory portion of the respiratory flow waveform, also referred to as length of inhalation or length of inspiration.

Exhalation time (Te): The duration of the expiratory portion of the respiratory flow waveform, also referred to as length of exhalation or length of expiration.

Total time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

5.9.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.9. Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Plenum chamber: a mask plenum chamber will be taken to a mean portion of a patient interface having walls enclosing a volume of space, the volume having air therein pressurised above atmospheric pressure in use. A shell may form part of the walls of a mask plenum chamber. In one form, a region of the patient's face forms one of the walls of the plenum chamber.

5.10 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a". "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

6 CITATIONS

6.1 Non-Patent Literature

Lorino, A. M., H. Lorino, and A. Harf, *A synthesis of the Otis, Mead, and Mount mechanical respiratory models*. Respiration Physiology. 97(2): p. 123-133.

Rodarte, J. R. and K. Rehder, *Dynamics of Respiration*, in *Handbook of Physiology—The Respiratory System*. 2011. Williams and Wilkins: Baltimore, p. 131-144.

*Handbook of Physiology—The Respiratory System*, ed. J. West. 2012: John Wiley & Sons, Inc.

The invention claimed is:

1. An apparatus for controlling a supply of breathable gas at a positive pressure for amelioration or treatment of a respiratory disorder comprising:
    a controller configured to:
        control a therapy apparatus for providing a supply of breathable gas, the therapy apparatus configured to couple with a patient interface to deliver the supply of breathable gas to an airway of a patient, the patient interface including (a) a valve configured to selectively block and unblock fluid communication between (i) a blower and a sensor of the therapy apparatus and (ii) the patient interface, and (b) a vent to exhaust a flow of exhaust gas from the patient interface,
        determine an expiratory characteristic based on a measure that is obtained from the sensor while the fluid communication is unblocked, and
        adjust a first pressure in the patient interface while the fluid communication is blocked by the valve based on the expiratory characteristic by controlling the valve, wherein the valve is controlled by changing motor speed of the blower.

2. The apparatus as claimed in claim 1, further comprising the valve, the valve further comprising a movable portion to selectively block and unblock the fluid communication between the blower and the sensor with the patient interface.

3. The apparatus as claimed in claim 2, wherein the movable portion is configured to be movable by a pressure difference acting on the movable portion.

4. The apparatus as claimed in claim 3, wherein the movable portion comprises a membrane.

5. The apparatus as claimed in claim 1, wherein the expiratory characteristic is an estimate of expiratory flow rate, an estimate of pressure in the patient interface or a phase of expiration.

6. The apparatus as claimed in claim 1, wherein the expiratory characteristic is determined based on an expiratory flow model comprising one or a combination of a look-up table or a mathematical relationship.

7. The apparatus as claimed in claim 1, wherein the blower is configured to generate the supply of breathable gas at a second pressure as an output to adjust the valve such that the first pressure is adjusted by changing the second pressure.

8. The apparatus as claimed in claim 1, wherein the expiratory characteristic is determined based on one or more of: a ventilation volume, a tidal volume, a peak inspiratory flow, a length of time in inspiration, a lung compliance, a lung resistance, an end of inspiration or a start of expiration.

9. The apparatus as claimed in claim 1, wherein the expiratory characteristic is determined using a measure of respiration.

10. An apparatus for controlling a supply of breathable gas at a positive pressure for treatment of a respiratory disorder, the apparatus comprising:
    a controller, including at least one processor, the controller configured to:
        control a blower of a therapy apparatus for providing a supply of breathable gas at a controlled pressure above ambient in a patient interface, the controller coupled with at least one sensor for the therapy apparatus, the at least one sensor configured to measure pressure through a conduit from the therapy apparatus to the patient interface, the conduit in fluid communication with the patient interface, the patient interface configured to deliver the supply of breathable gas to an airway of a patient, and
        determine a value estimating a gas pressure in the patient interface during cyclical blocking and unblocking of the conduit to the at least one sensor, the determination of the value estimating the gas pressure in the patient interface including Ian unblocked-conduit process for determining the value estimating the gas pressure in the patient interface during an unblocked condition of the conduit to the at least one sensor based on the pressure measured by the at least one sensor and (ii) a blocked-conduit process for determining the value estimating the gas pressure in the patient interface during a blocked condition of the conduit to the at least one sensor, wherein in the blocked-conduit process, the controller is configured to determine the value estimating the gas pressure in the patient interface without using measurements from the at least one sensor in the blocked condition,
    wherein the controller controls the blower of the therapy apparatus to adjust the controlled pressure of the breathable gas based on the determined value estimating the gas pressure in the patient interface and a target pressure.

11. The apparatus of claim 10 wherein the unblocked-conduit process determines the value estimating the gas pressure in the patient interface from a current measure of pressure from the sensor during unblocking of the conduit to the at least one sensor.

12. The apparatus of claim 11 wherein the unblocked-conduit process determines a pressure adjustment for pressure in the patient interface from a difference between the determined value estimating the gas pressure in the patient interface and the target pressure.

13. The apparatus of claim 10 wherein the blocked-conduit process determines the value estimating the gas pressure in the patient interface from a modelled flow estimate, during blocking of the conduit to the at least one sensor.

14. The apparatus of claim 13 wherein modelled flow estimate is an estimate of expiratory flow.

15. The apparatus of claim 14 wherein the determined value estimating the gas pressure in the patient interface is calculated from an elapsed time and the expiratory flow estimate.

16. The apparatus of claim 15 wherein the blocked-conduit process determines the elapsed time by detecting an end of inspiration.

17. The apparatus of claim 10 wherein the controller is further configured for cyclical selection of the unblocked-conduit process to determine the value estimating the gas pressure in the patient interface or the blocked-conduit process to determine the value estimating the gas pressure in the patient interface.

18. The apparatus of claim 17 wherein the controller is further configured to select the unblocked-conduit process to determine the value estimating the gas pressure in the patient interface upon determination of patient inspiration.

19. The apparatus of claim 17 wherein the controller is further configured to select the blocked-conduit process to determine the value estimating the gas pressure in the patient interface upon determination of patient expiration.

20. The apparatus of claim 10 wherein the controller is further configured to determine an unintentional leak flow by subtracting a magnitude of a patient flow at a determined point of inflection created by switching from expiration to inspiration from a total flow.

21. The apparatus of claim 10 further comprising the therapy apparatus including the blower and the at least one sensor.

22. The apparatus of claim 10 further comprising the patient interface, the conduit and a valve configured to selectively block expiratory gas communication to the at least one sensor.

23. A method of controlling a blower of a therapy apparatus for providing a supply of breathable gas to a patient interface at a controlled pressure, the method comprising:
with a sensor of the therapy apparatus, measuring a pressure through a conduit from the therapy apparatus to the patient interface, the conduit in fluid communication with the patient interface; and
determining in an unblocked-conduit process and a blocked-conduit process a value estimating a patient interface gas pressure for controlling the blower during blocking and unblocking of the conduit to the sensor, wherein the unblocked-conduit process determines the value estimating patient interface gas pressure during an unblocked condition of the conduit to the sensor based on the pressure measured by the sensor and the blocked-conduit process determines the value estimating patient interface gas pressure during a blocked condition of the conduit to the sensor, wherein the blocked-conduit process determines the value estimating patient interface gas pressure without using measurements from the sensor in the blocked condition,
wherein the pressure of the breathable gas is adjusted based on the determined value estimating patient interface gas pressure and a target pressure.

24. The method of claim 23 wherein the unblocked-conduit process determines the value estimating patient interface gas pressure from a current measure of pressure from the sensor during unblocking of the conduit to the sensor.

25. The method of claim 24 wherein the unblocked-conduit process determines the value estimating patient interface gas pressure from a pressure drop associated with a delivery conduit characteristic and the current measure of pressure.

26. The method of claim 24 wherein the unblocked-conduit process determines a pressure adjustment for pressure in the patient interface from a difference between the determined value estimating patient interface gas pressure and the target pressure.

27. The method of claim 23 wherein the blocked-conduit process determines the value estimating patient interface gas pressure from a modelled flow estimate during blocking of the conduit to the sensor.

28. The method of claim 27 wherein the blocked-conduit process determines a pressure adjustment for pressure in the patient interface from a difference between the determined value estimating patient interface gas pressure and the target pressure.

29. The method of claim 23 further comprising cyclically selecting the unblocked-conduit process and the blocked-conduit process, wherein the unblocked-conduit process is selected upon determination of patient inspiration and the blocked-conduit process is selected upon determination of patient expiration.

* * * * *